US011532087B2

(12) United States Patent
Ambwani et al.

(10) Patent No.: US 11,532,087 B2
(45) Date of Patent: Dec. 20, 2022

(54) STENT DETECTION METHODS AND IMAGING SYSTEM INTERFACES

(71) Applicant: LightLab Imaging, Inc., Westford, MA (US)

(72) Inventors: Sonal Ambwani, Hopkinton, MA (US); Christopher E. Griffin, Wilton, NH (US); James G. Peterson, Yarmouth, ME (US); Satish Kaveti, Sharon, MA (US); Joel M. Friedman, Andover, MA (US)

(73) Assignee: LightLab Imaging, Inc., Westford, MA (US)

( * ) Notice: Subject to any disclaimer, the term of this patent is extended or adjusted under 35 U.S.C. 154(b) by 148 days.

(21) Appl. No.: 17/155,778

(22) Filed: Jan. 22, 2021

(65) Prior Publication Data

US 2021/0217175 A1 Jul. 15, 2021

Related U.S. Application Data

(63) Continuation of application No. 16/166,520, filed on Oct. 22, 2018, now Pat. No. 10,902,599, which is a
(Continued)

(51) Int. Cl.
*G06T 7/11* (2017.01)
*A61B 34/20* (2016.01)
(Continued)

(52) U.S. Cl.
CPC ............... *G06T 7/11* (2017.01); *A61B 34/20* (2016.02); *G06T 7/0012* (2013.01); *G06T 7/174* (2017.01);
(Continued)

(58) Field of Classification Search
CPC ............... G06T 7/0012; G06T 7/0042; G06T 2207/10101; G06T 2207/30101;
(Continued)

(56) References Cited

U.S. PATENT DOCUMENTS

| | | |
|---|---|---|
| 4,548,473 A | 10/1985 | Lo et al. |
| 5,054,492 A | 10/1991 | Scribner et al. |

(Continued)

FOREIGN PATENT DOCUMENTS

| | | |
|---|---|---|
| CA | 2887360 A1 | 4/2014 |
| CN | 101264014 A | 9/2008 |

(Continued)

OTHER PUBLICATIONS

Wang et al, "Automatic stent strut detection in intravascular optical coherence tomographic pullback runs", Int. J. Cardiovase Imaging, 2013. (Year: 2013).*

(Continued)

*Primary Examiner* — Ruiping Li
(74) *Attorney, Agent, or Firm* — Lerner, David, Littenberg, Krumholz & Mentlik, LLP

(57) ABSTRACT

The disclosure relates, in part, to computer-based visualization of stent position within a blood vessel. A stent can be visualized using intravascular data and subsequently displayed as stent struts or portions of a stent as a part of a one or more graphic user interface(s) (GUI). In one embodiment, the method includes steps to distinguish stented region(s) from background noise using an amalgamation of angular stent strut information for a given neighborhood of frames. The GUI can include views of a blood vessel generated using distance measurements and demarcating the actual stented region(s), which provides visualization of the stented region. The disclosure also relates to display of intravascular diagnostic information such as indicators. An indicator can
(Continued)

be generated and displayed with images generated using an intravascular data collection system. The indicators can include one or more viewable graphical elements suitable for indicating diagnostic information such as stent information.

20 Claims, 27 Drawing Sheets
(22 of 27 Drawing Sheet(s) Filed in Color)

Related U.S. Application Data continuation of application No. 15/157,340, filed on May 17, 2016, now Pat. No. 10,109,058, which is a continuation-in-part of application No. 14/975,516, filed on Dec. 18, 2015, now Pat. No. 9,996,921.

(60) Provisional application No. 62/322,578, filed on Apr. 14, 2016, provisional application No. 62/196,997, filed on Jul. 25, 2015, provisional application No. 62/162,795, filed on May 17, 2015.

(51) Int. Cl.
*G06T 7/174* (2017.01)
*G06T 7/00* (2017.01)
*G06V 10/50* (2022.01)

(52) U.S. Cl.
CPC .... *G06V 10/507* (2022.01); *A61B 2034/2065* (2016.02); *G06T 2200/24* (2013.01); *G06T 2207/10068* (2013.01); *G06T 2207/10101* (2013.01); *G06T 2207/30021* (2013.01); *G06T 2207/30052* (2013.01); *G06T 2207/30101* (2013.01); *G06V 2201/03* (2022.01)

(58) Field of Classification Search
CPC ........ G06T 2207/20076; A61B 5/0066; A61B 5/6852; A61B 5/0086; A61B 5/05
USPC .......................................................... 382/182
See application file for complete search history.

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Corl et al. |
| 5,748,598 A | 5/1998 | Swanson et al. |
| 5,771,895 A | 6/1998 | Stager |
| 5,784,352 A | 7/1998 | Swanson et al. |
| 5,797,849 A | 8/1998 | Vesely et al. |
| 5,822,391 A | 10/1998 | Whitting |
| 5,908,415 A | 6/1999 | Sinofsky |
| 5,921,931 A | 7/1999 | O'Donnell et al. |
| 5,947,959 A | 9/1999 | Sinofsky |
| 5,956,355 A | 9/1999 | Swanson et al. |
| 5,965,355 A | 10/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,048,716 B1 | 5/2006 | Kucharczyk et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |

(56) References Cited

U.S. PATENT DOCUMENTS

| | | |
|---|---|---|
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,412,312 B2 | 4/2013 | Judell et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,670,603 B2 | 3/2014 | Tolkowsky et al. |
| 8,687,201 B2 | 4/2014 | Adler |
| 8,693,756 B2 | 4/2014 | Tolkowsky et al. |
| 8,700,130 B2 | 4/2014 | Iddan et al. |
| 8,750,615 B2 | 6/2014 | Rollins et al. |
| 8,781,193 B2 | 7/2014 | Steinberg et al. |
| 8,786,336 B1 | 7/2014 | Schmitt |
| 8,831,321 B1 | 9/2014 | Elbasiony |
| 8,855,744 B2 | 10/2014 | Tolkowsky et al. |
| 8,909,323 B2 | 12/2014 | Baumgart |
| 8,913,084 B2 | 12/2014 | Chen et al. |
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony et al. |
| 9,308,052 B2 | 4/2016 | Tolkowsky et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,488,464 B1 | 11/2016 | Schmitt |
| 9,629,571 B2 | 4/2017 | Tolkowsky et al. |
| 2002/0115931 A1 | 8/2002 | Strauss et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0049672 A1 | 3/2005 | Murphy |
| 2005/0201662 A1 | 9/2005 | Petersen et al. |
| 2005/0238067 A1 | 10/2005 | Choi |
| 2005/0249391 A1 | 11/2005 | Kimmel et al. |
| 2006/0095065 A1 | 5/2006 | Tanimura et al. |
| 2006/0135870 A1 | 6/2006 | Webler |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0024617 A1 | 2/2007 | Poole |
| 2007/0055132 A1 | 3/2007 | Camus et al. |
| 2007/0060822 A1 | 3/2007 | Alpert et al. |
| 2007/0066890 A1 | 3/2007 | Maschke |
| 2007/0115481 A1 | 5/2007 | Toth et al. |
| 2007/0123771 A1 | 5/2007 | Redel et al. |
| 2007/0135803 A1 | 6/2007 | Belson |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2007/0260198 A1 | 11/2007 | Atlas |
| 2007/0293932 A1 | 12/2007 | Zilla et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt |
| 2008/0177139 A1 | 7/2008 | Courtney et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0228086 A1 | 9/2008 | Ilegbusi et al. |
| 2008/0281205 A1 | 11/2008 | Naghavi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0264768 A1 | 10/2009 | Courtney et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0142785 A1 | 6/2010 | Dahnke et al. |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank |
| 2010/0232672 A1 | 9/2010 | Jandt et al. |
| 2010/0253949 A1 | 10/2010 | Adler et al. |
| 2011/0007315 A1 | 1/2011 | Petersen et al. |
| 2011/0034814 A1 | 2/2011 | Kopperschmidt |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1 | 9/2011 | Eichler |
| 2011/0257545 A1 | 10/2011 | Suri |
| 2011/0263960 A1 | 10/2011 | Mitchell |
| 2011/0319752 A1 | 12/2011 | Steinberg et al. |
| 2012/0004529 A1 | 1/2012 | Tolkowsky et al. |
| 2012/0029339 A1 | 2/2012 | Cohen et al. |
| 2012/0057157 A1 | 3/2012 | Petersen et al. |
| 2012/0075638 A1 | 3/2012 | Rollins et al. |
| 2012/0130243 A1 | 5/2012 | Balocco et al. |
| 2012/0162660 A1 | 6/2012 | Kemp |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2012/0310081 A1 | 12/2012 | Adler et al. |
| 2012/0316433 A1 | 12/2012 | Maruyama |
| 2012/0316491 A1 | 12/2012 | Jonsson |
| 2012/0323311 A1 | 12/2012 | McClain et al. |

(56) References Cited

U.S. PATENT DOCUMENTS

| | | |
|---|---|---|
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0100440 A1 | 4/2014 | Cheline et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0146950 A1 | 5/2014 | Chida et al. |
| 2014/0163664 A1 | 6/2014 | Goldsmith |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0257087 A1 | 9/2014 | Elbasiony et al. |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0286541 A1 | 9/2014 | Kiyomizu et al. |
| 2014/0309536 A1 | 10/2014 | Douk et al. |
| 2014/0316758 A1 | 10/2014 | Yagi et al. |
| 2014/0379269 A1 | 12/2014 | Schmitt |
| 2015/0119707 A1 | 4/2015 | Schmitt |
| 2015/0153157 A1 | 6/2015 | Schmitt et al. |
| 2015/0190054 A1 | 7/2015 | Kaneko |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1 | 3/2016 | Svanerudh |
| 2016/0066880 A1 | 3/2016 | Stigall et al. |
| 2016/0070066 A1 | 3/2016 | Schmitt et al. |
| 2016/0073885 A1 | 3/2016 | Adler |
| 2016/0166232 A1 | 6/2016 | Merritt |
| 2016/0174925 A1 | 6/2016 | Dascal et al. |
| 2016/0292857 A1 | 10/2016 | Begin et al. |
| 2016/0313507 A1 | 10/2016 | Adler et al. |
| 2016/0335763 A1 | 11/2016 | Ambwani et al. |
| 2016/0335766 A1 | 11/2016 | Ambwani et al. |

FOREIGN PATENT DOCUMENTS

| | | |
|---|---|---|
| CN | 101779222 A | 7/2010 |
| CN | 102014984 A | 4/2011 |
| CN | 102046071 A | 5/2011 |
| CN | 102802492 A | 11/2012 |
| CN | 103619256 A | 3/2014 |
| CN | 104063679 A | 9/2014 |
| EP | 1833363 A2 | 9/2007 |
| EP | 2062526 A1 | 5/2009 |
| EP | 2713858 A1 | 4/2014 |
| EP | 3053505 A1 | 8/2016 |
| JP | S63127201 A | 5/1988 |
| JP | 2012505669 A | 3/2012 |
| JP | 2013505782 A | 2/2013 |
| JP | 2013154192 A | 8/2013 |
| JP | 2014158619 A | 9/2014 |
| JP | 2014525761 A | 10/2014 |
| KR | 20140092102 A | 7/2014 |
| WO | 0122870 A1 | 4/2001 |
| WO | 2006076409 A2 | 7/2006 |
| WO | 2007002685 A2 | 1/2007 |
| WO | 2011038044 A2 | 3/2011 |
| WO | 2012126070 A1 | 9/2012 |
| WO | 2012166332 A1 | 12/2012 |
| WO | 2012176191 A1 | 12/2012 |
| WO | 2013049123 A1 | 4/2013 |
| WO | 2013175472 A2 | 11/2013 |
| WO | 2014002095 A2 | 1/2014 |
| WO | 2014045327 A1 | 3/2014 |
| WO | 2014137353 A1 | 9/2014 |
| WO | 2014175853 A1 | 10/2014 |
| WO | 2015044987 A1 | 4/2015 |

OTHER PUBLICATIONS

Unal, et al, "Shape-Driven Segmentation of the Arterial Wall in Intravascular Ultrasound Images", IEEE, 2008. (Year: 2008).*

Chinese Search Report for Application No. 201680049576.4, dated Jul. 5, 2021, 7 pages.

Li Y, Gutiérrez-Chico JL, Holm NR, Yang W, Hebsgaard L, Christiansen EH, Mæng M, Lassen JF, Yan F, Reiber JH, Tu S. Impact of side branch modeling on computation of endothelial shear stress in coronary artery disease: coronary tree reconstruction by fusion of 3D angiography and OCT. Journal of the American College of Cardiology. Jul. 14, 2015;66(2):125-35.

Search Report from Third Office Action for Chinese Application No. 201680048506.7 dated Jul. 1, 2021; 3 pages.

Wang et al., Biomedical Optics Express "Fully automated side branch detection in intravascular optical coherence tomography pullback runs" Aug. 2014, pp. 3160-3173, vol. 5 No. 9.

Extended European Search Report issued in Appln. No. 21203928.3 dated Apr. 7, 2022 (7 pages).

Chinese Search Report for International Application No. 201680036611.9, dated Mar. 1, 2021, 8 pages.

Bonnema et al., "An automatic algorithm for detecting stent endothelialization from volumetric optical coherence tomography datasets", Physics in Medicine and Biology, 53 :12, Jun. 21, 2008, pp. 3083-3098.

Briguori et al., "Intravascular ultrasound criteria for the assessment of the functional significance of intermediate coronary artery stenoses and comparison with fractional flow reserve," Am J. Cardiol 87:136-141, 2001.

Dave Fornell, "The Advantages and Disadvantages of OCT vs. IVUS", Diagnostic and Interventional Cardiology, May 18, 2011, pp. 1-4.

Gabriele Alex et al: "Reproducibility of the Carpet View system: a novel technical solution for display and off line analysis of OCT images", International Journal of Cardiovascular Imaging, Kluwer Academic Publishers, Dordrecht, NL, vol. 30, No. 7, Jun. 14, 2014 (Jun. 14, 2014), pp. 1225-1233, XP035393911, ISSN: 1569-5794, DOI: 10.1007/810554-014-0464-2 [retrieved on Jun. 14, 2014].

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Hariri et al., "An automatic image processing algorithm for initiating and terminating intracoronary OFDI pullback" Biomedical Optics Express 1:2 566-573 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Herrington et al., "Semi-automated boundary detection for intravascular ultrasound," Computers in Cardiology 1992 Proceedings., pp. 103-106, Oct. 1992.

International Search Report and Written Opinion for International application No. PCT/US2016/032933 mailed from International Searching Authority dated Aug. 1, 2016 (14 pages).

(56) References Cited

OTHER PUBLICATIONS

International Search Report and Written Opinion of the International Searching Authority for International application No. PCT/US2016/032908, dated Sep. 23, 2016 (13 pages).
Kassab et al., "The pattern of coronary arteriolar bifurcations and the uniform shear hypothesis," Annals of Biomedical Engineering 23 (1): 13-20, 1995.
Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.
Kolyva et al, "Increased diastolic time fraction as beneficial adjunct of a1-adrenergic receptor blockade after percutaneous coronary intervention," Am J Physiol Heart Circ Physiol 295: H2054-H2060, 2008.
Kolyva et al., "'Windkesselness' of coronary arteries hampers assessment of human coronary wave speed by single-point technique," Am J Physiol Heart Circ Physiol, 295: H482-H490, 2008.
Kovalski et al., "Three-dimensional automatic quantitative analysis of intravascular ultrasound images," Ultrasound in Medicine & Biology, 26(4):527-537, 2000.
Laslett, "Normal left main coronary artery diameter can be predicted from diameters of its branch vessels," Clinical Cardiology 18 (10): 580-582, 1995.
Mojsilovic et al., "Automatic segmentation of intravascular ultrasound images: A texture-based approach," Annals of Biomedical Engineering, 25:1059-1071, Nov. 1997.
Ofili et al., "Differential characterization of blood flow, velocity, and vascular resistance between proximal and distal normal epicardial human coronary arteries: analysis by intracoronary Doppler spectral flow velocity," Am Heart J .30:137-46, 1995.
Ohta et al, "Rheological Changes After Stenting of a Cerebral Aneurysm: A Finite Element Modeling Approach," Cardiovascular and Interventional Radiology (2005) 28:768-772.
Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.
Perez-Rovira et al., "Deformable Registration of Retinal Fluorescein Angiogram Sequences Using Vasculature Structures", 32nd Annual Cont. of IEEE EMBS, 2010, pp. 4383-4386.
Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.
Pujol et al., "Intravascular Ultrasound Images Vessel Characterization using AdaBoost," Functional Imaging and Modeling of the Heart: Lecture Notes in Computer Science, pp. 242-251, 2003.
Seiler et al., "Basic structure-function relations of the epicardial coronary vascular tree, Basis of quantitative coronary arteriography for diffuse coronary artery disease," Circulation 85 (6): 1987-2003, 1992.
Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012)28:1315-1327.
Siebes et al, "Single-wire pressure and flow velocity measurement to quantify coronary stenosis hemodynamics and effects of percutaneous interventions," Circulation 109:756-762, 2004.
Sihan et al., "A Novel Approach to Quantitative Analysis of Intravascular Optical Coherence Tomography Imaging," Computers in Cardiology 2008; 35:1089-1092.
Sihan et al., "Fully Automatic Three-Dimensional Quantitative Analysis of Intracoronary Optical Coherence Tomography: Method and Validation," Catheterization and Cardiovascular Interventions 74:1058-1065 (2009).
Sonka et al., "Segmentation of intravascular ultrasound images: a knowledge-based approach," IEEE Transactions on Medical Imaging, 14(4):719-732, Dec. 1995.
Span, "Coronary Blood Flow," Ch 12. Dordrecht, The Netherlands: Kluwer Acedemic Publishers, Boston; 1991: pp. 333-361.
Takagi et al., "Clinical potential of intravascular ultrasound for physiological assessment of coronary stenosis," Circulation 100: 250-255, 1999.
Takano et al . . . "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.
Taki et al., "Automatic segmentation of calcified plaques and vessel borders in IVUS images," International Journal of Computer Assisted Radiology and Surgery, 3(3-4):347-354, Sep. 2008.
Tung et al., "Automatic Detection of Coronary Stent Struts in Intravascular OCT Imaging," Proceedings of SPIE, vol. 8315, Feb. 22, 2012 (8 pgs.).
Unal et al., "Stent implant follow-up in intravascular optical coherence tomography images," Int J Cardiovasc Imaging, DOI 10.1007/s10554-009-9508-4, published online Sep. 24, 2009, 8 pgs.
Van den Berg et al., "Using three-dimensional rotational angiography for sizing of covered stents," Am. J. Roentgenology, 178:149-152 (2002).
Verhoeff et al., "Influence of percutaneous coronary intervention on coronary microvascular resistance index," Circulation 111:76-82, 2005.
Wang et al: "Automatic stent strut detection in intravascular optical coherence tomographic pullback runs", Int. J. Cardiovasc Imaging, 2013 (Year: 2013).
Wang, et al., "3D Assessment of Stent Cell Size and Side Branch Access in Intravascular Optical Coherence Tomographic Pullback Runs," Computerized Medical Imaging and Graphics, Mar. 2014, pp. 113-122, vol. 38, No. 2.
White et al., "Does visual interpretation of the coronary angiogram predict the physiologic importance of coronary stenoses?," N. Engl J Med 310:13 819-824, 1984.
Wilson et al., "Prediction of the physiologic significance of coronary arterial lesions by quantitative lesion geometry in patients with limited coronary artery disease," Circulation 75: 723-732, 1987.
Wong et al., "A novel method of coronary stent sizing using intravascular ultrasound: safety and clinical outcomes," Int J. Angiol. , 18(1): 22-24 2009.
Xu et al., "Characterization of atherosclerosis plaques by measuring both backscattering and attenuation coefficients in optical coherence tomography," Journal of Biomedical Optics, 13:3, May/Jun. 2008, 8 pgs.

* cited by examiner

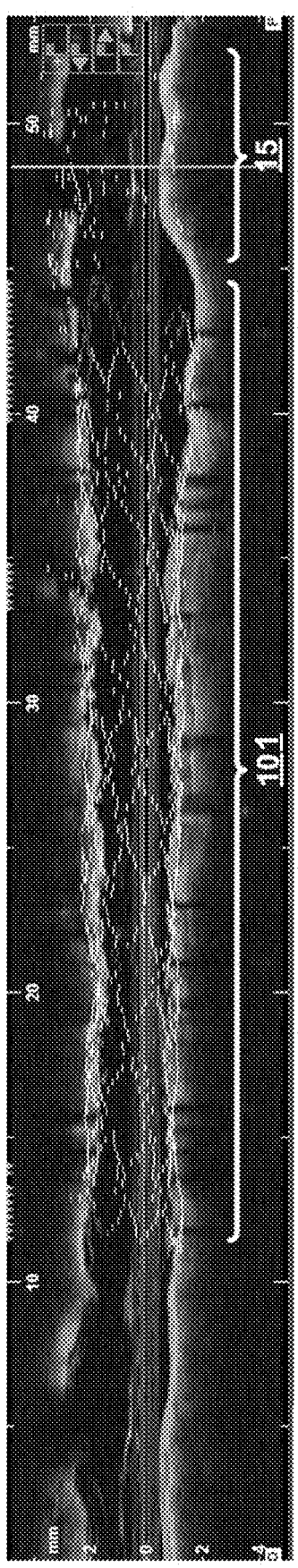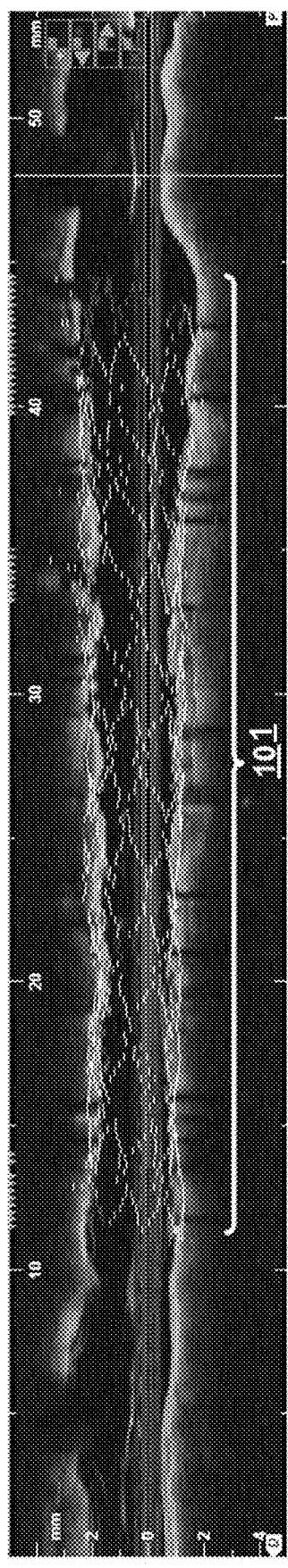
FIG. 14A
FIG. 14B

STENT DETECTION METHODS AND IMAGING SYSTEM INTERFACES

CROSS-REFERENCE TO RELATED APPLICATIONS

This application is a continuation of U.S. application Ser. No. 16,166,520, filed Oct. 22, 2018, which is a continuation of U.S. application Ser. No. 15/157,340, which claims priority to and the benefit of U.S. Provisional Patent Application No. 62/162,795 filed on May 17, 2015, U.S. Provisional Patent Application No. 62/196,997 filed on Jul. 25, 2015, U.S. Provisional Patent Application No. 62/322,578 filed on Apr. 14, 2016, and which also is a continuation-in-part of U.S. patent application Ser. No. 14/975,516 filed on Dec. 18, 2015, the disclosures of which are each herein incorporated by reference in their entirety.

FIELD OF THE INVENTION

The disclosure relates generally to intravascular measurements and feature detection and related diagnostic methods and devices.

BACKGROUND OF THE INVENTION

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease. OCT images provide high-resolution visualization of coronary artery morphology and can be used alone or in combination with other information such as angiography data and other sources of subject data to aid in diagnosis and planning such as stent delivery planning.

OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be deployed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel. Angiography systems, intravascular ultrasound systems, OCT systems, in combinations or alone can be used to facilitate stent delivery planning and stent deployment.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel if the portions of the stent fail to contact the vessel wall, the risk of thrombosis may increase. An underinflated or malapposed stent may fail to restore normal flow. Once a stent is installed, stent malapposition and under expansion of the stent can result in various problems.

There are other challenges associated with stent placements and related procedures. Visualizing a stent deployment relative to the wall of a blood vessel using an angiography system is challenging to undertake by inspection. Further, reviewing angiography images manually to determine stent position on a per image basis is also prone to error.

In addition, after deploying a stent, a clinician may image the treatment site to confirm that a stent has been properly deployed. However, background noise caused by, for example, uncleared blood cells, can appear as stent struts in OCT image data, making it difficult to accurately detect the stent. Sometimes, the clinician can identify the stented region, but requiring user intervention results in significant variability, is subject to user error, and significantly increases the length of the procedure. In addition, different stents can have different geometries and mesh patterns which can complicate their evaluation.

The present disclosure addresses these challenges and others.

BRIEF SUMMARY OF THE INVENTION

In part, the disclosure relates to angiography and intravascular data collection systems such as OCT and/or IVUS that can be used to plan stent delivery or otherwise generate and display diagnostic information of interest. The disclosure also relates to the generation of various indicators and the integration of them relative to displays of image data. As an example, a longitudinal indicator such as an apposition bar can be used alone or in conjunction with a stent strut indicator and overlaid on angiography frames co-registered with an intravascular data set such as a set of OCT scan lines or images generated with respect thereto for diagnostic processes such as stent planning.

In part, the disclosure relates to systems and methods for displaying the results of data analysis applied to an intravascular data set to the user of an intravascular data collection system and on angiography system in one embodiment. In part, this disclosure describes a graphic user interface (GUI) that provides user interface and graphic data representations that can be applied to one or more generated images of a vessel or angiography images such that regions of interest such as areas of stent apposition and others are easy to find and understand on OCT and angiography images.

In part, the disclosure relates to a data collection system such as an intravascular data collection system suitable for use in cath lab such as an optical coherence tomography system. In part, the disclosure relates to a data collection system that includes a processor suitable for displaying intravascular image data. The image data displayed includes data or images generated based upon depth measurements. In one embodiment, the image data is generated using optical coherence tomography. The system can also display a user interface for display of intravascular information such as data relating to stent malapposition in a longitudinal mode on a per stent strut basis or as a bar having regions corresponding to stent, no stent, or stent apposition levels of potential interest for one or more stents in a vessel.

One or more indicators such as longitudinal indicators, as a non-limiting example, can be generated in response to stent detection processing and lumen boundary detection and displayed relative to angiography, OCT, and IVUS images. These can be viewed by a user to plan stent delivery and to inflate or adjust a stent delivery by reviewing a co-registered OCT image and an angiography image with the relevant indicators of interest. In part, the systems and methods described herein relate to methods of avoiding or reducing likelihood of data misinterpretations by replacing regions of missing data with an indicator such as hashing, a colored region, or other visual indicator. In this way, an end user is informed when data is missing rather than misconstrue a black region as a shadow or side branch. Thus, a missing data region is coded with an indicator that prevents that region from being misconstrued as a sidebranch, stent or other feature of interest to a diagnostician. In one embodiment, the methods can include the step of displaying an indicia of a stent strut on a graphical user interface and displaying an indicia indicative of one or more regions in an intravascular image wherein data was unavailable for display. In one embodiment, an apposition bar is displayed such that it is intravascular view independent such that the apposition bar is displayed when no indicator or stent containing image is present. In one embodiment, the disclosure relates to an apposition bar aligned with a stent region, the stented region includes the located stent strut, wherein the apposition bar is rotationally agnostic or persistent.

In part, the disclosure relates to stent detection and shadow detection in the context of intravascular data sets obtained using a probe such as, for example, and optical coherence tomography probe or an intravascular ultrasound probe.

In part, the disclosure relates to systems and methods for precise identification of metal stent strut offsets, or locations, within shadows cast in OCT image data. Methods of stent strut detection can include accessing a plurality of frames of intravascular imaging data, the plurality of frames comprising optical coherency tomography (OCT) scan lines, identifying a shadow region corresponding to a candidate stent strut, identifying scan lines that correspond to a candidate stent strut shadow region to generate candidate strut shadow scan lines, and analyzing the candidate strut shadow scan lines to identify the location of a stent strut.

Methods of stent strut detection also can include storing a plurality of frames of intravascular imaging data, detecting stent struts in a first group of frames of the plurality of frames, detecting one or more shadow regions in the first group of frames, wherein one or more of the shadow regions is adjacent to a detected stent strut, determining on a per shadow region basis if a given shadow region is a guidewire induced region or a side branch induced region to generate a set of candidate stent strut shadow regions, wherein each candidate stent strut shadow region comprises a shadow boundary, and identifying scan lines of a candidate stent strut shadow region within the shadow boundary.

Methods of the invention can include additional steps or features. For example, the methods can include identifying a shadow region corresponding to a candidate stent strut by eliminating shadow regions corresponding to non-stent features. The non-stent features can be selected, for example, from the group consisting of: a guidewire, a side branch, and combinations thereof.

The methods can include eliminating candidate strut shadow scan lines that contain spillage from lumen pixels. The methods can include determining a projection across each of the candidate strut shadow scan lines by summing a signal response across the candidate strut shadow scan lines, or a portion or sample of the scan lines. The methods can include identifying up to three local maxima in the projection.

The methods can include ranking local maxima based on peak signal intens to generate a peak score. The ranking can be an ordinal ranking, with local maxima having higher peak signal intensity receiving a higher peak score.

The methods can include ranking the local maxima based on proximity to the blood vessel wall to generate a proximity score. The ranking can be an ordinal ranking, with local maxima closer to the blood vessel wall receiving a higher proximity score. The methods can include assigning a malapposition score to each local maxima. The malapposition score can be binary, with malapposed local maxima receiving a score of zero.

The methods can include summing the peak score, the proximity score, and the malapposition score, wherein the local maximum with the highest total score is designated as the location of the stent strut.

The methods can include identifying a plurality shadow region corresponding to a candidate stent strut, identifying scan lines that correspond to each candidate stent strut shadow region, and identifying, within each candidate stent strut shadow region, the location of a stent strut. The methods can include performing a cross-frame analysis to validate designated stent struts across multiple optical coherence tomography (OCT) imaging frames.

In part, the disclosure relates to intravascular data collection systems and angiography systems and the exchange of data between two or more of the foregoing and the generation and display of diagnostic information such as indicators. One or more indicators can be generated and displayed such as by overlaying or otherwise combining such indicators with images generated using an intravascular data collection system. The indicators can include longitudinal, cross-sectional, and other indictor types such as one more indicator or graphical elements suitable for indicating diagnostic information of interest. Indicators can be used to guide a user during stent delivery planning and other actions. The disclosure also relates to stent detection and shadow detection in the context of intravascular data sets obtained using a probe such as, for example, and optical coherence tomography probe or an intravascular ultrasound probe.

The present disclosure relates, in part, to computer-based visualization of stent position within a blood vessel. A stent can be visualized using OCT data and subsequently displayed as stent struts or portions of a stent as a part of a one or more graphic user interface(s) (GUI). Notably, the invention provides computer algorithms that distinguish stented region(s) from background noise. The GUI can include one or more views of a blood vessel generated using OCT distance measurements and demarcating the actual stented region(s), which provides visualization of the stented region.

In one embodiment, the disclosure relates to automated detection of one or more stent regions in a pullback. In one embodiment, an OCT, IVUS, or other intravascular modality is used to collect data during the pullback. In one embodiment, the disclosure relates to automatic detection of one or more stents in a given pullback and removal of false positive strut detections from frames not part of a stent. One object of some implementations described herein it to automatically detect the start and end frame of one or more stents in a given pullback without user input. The algorithm uses an angular metric as a threshold and frame-by-frame strut detections to determine which frame belong to a stent and which lie outside the stent regions.

The multi-frame processing algorithm automatically detects one or more stents in a pullback based on the struts detected during the single frame step. In this step, cross-frame information is brought in to identify the set of frames belonging to a particular stent and cleaning up false positives in non-stented regions. In one embodiment, the method includes the step of removing any detections in the guide catheter frames, determined after identifying position of the guide catheter.

In one embodiment, a one dimensional plot of angular coverage is used as a proxy or threshold for filtering stented from non-stent regions. If a frame does not have expected configuration, the angular coverage will be low and that be interpreted as the edge of the stent. The one dimensional plot is used for amalgamating data from one adjacent frame as a local neighborhood. In one embodiment, all of the struts in a multi-frame neighborhood come to together compute the coverage metric. Angles are measured for each strut detected in each frame. In a multi-frame algorithm (such as this), the angular position for the combined set of struts over a fixed neighborhood is used. In one embodiment, the method combines detected struts to create a super frame and then perform coverage analysis/filtering for stents on the super frame.

In one embodiment, even though struts from the neighborhood around frame k is used to compute the max angular gap and the angular coverage metric, they are assigned to frame k because that's where the neighborhood window is centered. In one embodiment, the angular metric threshold is on a per frame basis, neighborhood is one ahead of current frame and one frame behind the current frame. In one embodiment, the number of frames in a neighborhood on either side of a frame under review can include multiple frames without limitation.

In one embodiment, angles are measured for each strut detected in each frame. In a multi-frame algorithm implementation, the angular position for the combined set of struts over a fixed neighborhood is used. In one embodiment, a neighborhood of frames is processed relative to the angular metric threshold described herein and then a filtering process of the "in stented region signal" is performed using the threshold. In one embodiment, the neighborhood includes two frames. In one embodiment, the neighborhood includes three frames. In one embodiment, the neighborhood includes two or more frames.

In one embodiment, the disclosure relates to a non-transitory machine-readable memory medium encoded with a plurality of processor-executable instructions to perform a method of detecting a stented region in a blood vessel, comprising processor instructions to perform one or more of the steps described and depicted herein.

The invention relates, in part, to methods of detecting a stented region in a blood vessel. The method can include the steps of receiving optical coherence tomography data for a stented blood vessel, the optical coherence tomography data comprising a plurality of image frames; storing the optical coherence tomography data in a memory device of an intravascular data collection system; analyzing the plurality of image frames to identify stent struts on a per frame basis; demarcating an angular offset of identified stent struts to create amalgamated angular gap data over a neighborhood of frames of the plurality of image frames; and determining a maximum angular gap between any two adjacent struts in the neighborhood of frames.

The method can include one or more of the following features. The method can include classifying the frame as a stent-containing frame if the maximum angular gap is smaller than a threshold angular gap.

The method can include identifying zones that contain stents by identifying clusters of adjacent frames containing a maximum angular gap that is smaller than a threshold angular gap.

The method can include determining a centroid value for the stent blood vessel and computing the maximum angular gap relative to the vessel centroid for frame k. The maximum angular gap, $\theta_{max,k}$, for a given frame, k, is used to calculate an angular gap metric, $\Psi_k$, for frame k according to the formula $$\Psi_k = 1 - \frac{\theta_{maxk}}{2\pi}.$$

An angular gap metric closer to 1 is indicative of the frame containing a stent.

The method can include classifying the frame as a stent-containing frame if the angular gap metric is larger than a threshold angular gap (e.g., about 0.25 to about 0.65).

The method can include calculating the angular gap metric for frame k and at least one neighboring frame, k+1. The method can include iteratively calculating the angular gap metric for successive neighboring frames.

The method can include repeating one or more of the steps to sequentially classify a plurality of frames in the optical coherence tomography data. The method can include sequentially classifying frames as a stent-containing frame if the angular gap metric for a given frame is larger than a threshold angular gap. The method can include aggregating neighboring stent-containing frames into a stented region comprising a first frame and a last frame. The method can include terminating a first end of the stented region if a frame adjacent the first frame has an angular gap metric below the threshold angular gap.

The method can include terminating a second end of the stented region if a frame adjacent the last frame has an angular gap metric below the threshold angular gap. The disclosure also relates, in part, to methods of detecting a stented region in a stented blood vessel. The method can include the steps of storing, using an intravascular imaging system, one or more intravascular image datasets of the blood vessel, each intravascular dataset comprising a plurality of frames; storing, using an intravascular imaging system, one or more intravascular image datasets of the blood vessel, each intravascular dataset comprising a plurality of frames; defining a neighborhood, the neighborhood comprising a frame k and one or more frames in vicinity of frame k; determining an angular gap for frame k by combining all of struts detected on all frames of the neighborhood; and generating an angular coverage metric $\Psi_k$ with regard to frame k using the determined angular gap.

The angular coverage metric is of the form $$\Psi_k = 1 - \frac{\theta_{maxk}}{2\pi}$$

wherein, θmax,k is largest angular gap between adjacent struts.

The method can include sequentially classifying frames as a stent-containing frame if the angular coverage metric for a given frame is larger than a threshold angular gap. The disclosure also relates, in part, to a programmable processor-based computing device of an intravascular imaging system for detecting one or more stented regions. The programmable processor-based computing device can include one or more data access channels to receive intravascular imaging data; and a processor and associated memory in electrical communication with the one or more data access channels.

In one embodiment, the processor is programmed to store, using an intravascular imaging system, one or more intravascular image datasets of the blood vessel, each intravascular dataset comprising a plurality of frames; define a neighborhood, the neighborhood comprising a frame k and one or more frames in vicinity of frame k; determine an angular gap for frame k by combining all of the struts detected on all frames of the neighborhood; generate an angular coverage metric $\Psi_k$ with regard to frame k using the determined angular gap; and classify frames as a stent-containing frame if the angular coverage metric for a given frame is larger than a threshold angular gap.

In one embodiment, the disclosure relates to detecting the maximum stent malapposition distance, defined as the widest separation between the surface of the stent struts and the vessel wall over the entire length of the stent. Minimization of this distance, especially for drug-eluting stents, is necessary to assure that the stent is affixed firmly to the vessel wall and that the stent provides adequate radial support to prevent collapse of the vessel.

In one embodiment, the disclosure relates to detecting maximum stent malapposition distance, defined as the widest separation between the surface of the stent struts and the vessel wall over the entire length of the stent Minimization of this distance, especially for drug-eluting stents, is necessary to assure that the stent is affixed firmly to the vessel wall and that that the stent provides adequate radial support to prevent collapse of the vessel.

In part, the disclosure relates to a computer interface with a three dimensional depiction in the top panel of a stent that is not properly placed in the lumen of interest. Regions of stent malapposition can be shown as hatched regions or with other indicia. Thus, in one embodiment, the methods of the invention and features described herein are directed to a computer-based user interface that allows views of OCT in multiple panels. Further, stent malapposition can be shown in three-dimensions. In addition, in the case of stimulated stent placement, the user may reposition the stent to remove the areas of malapposition to simulate proper stent placement prior to implanting a stent in a real patient.

The methods can include displaying on a graphical user interface the validated stent struts. The disclosure also includes a computer readable medium comprising non-transitory instructions that when executed cause a processor to perform any of the foregoing steps.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation. Furthermore, although some aspects and embodiments are described using "means for" terminology, it is understood that all aspects, embodiments, and other concepts disclosed herein can serve as support for means plus function claims, even if specific "means for" language is not used in a specific portion of the written description.

BRIEF DESCRIPTION OF THE DRAWINGS

The patent or application file contains at least one drawing executed in color. Copies of this patent or patent application publication with color drawings) will be provided by the Office upon request and payment of the necessary fee.

The figures are not necessarily to scale, emphasis instead generally being placed upon illustrative principles. The figures are to be considered illustrative in all aspects and are not intended to limit the disclosure, the scope of which is defined only by the claims.

FIG. 14A is an intravascular image data representation user interface a stented vessel region before elimination of false positive stent struts in accordance with an illustrative embodiment of the disclosure.

FIG. 14B is an intravascular image data representation user interface of a stented vessel region after elimination of false positive stent struts in accordance with an illustrative embodiment of the disclosure.

DETAILED DESCRIPTION

Figure 1:
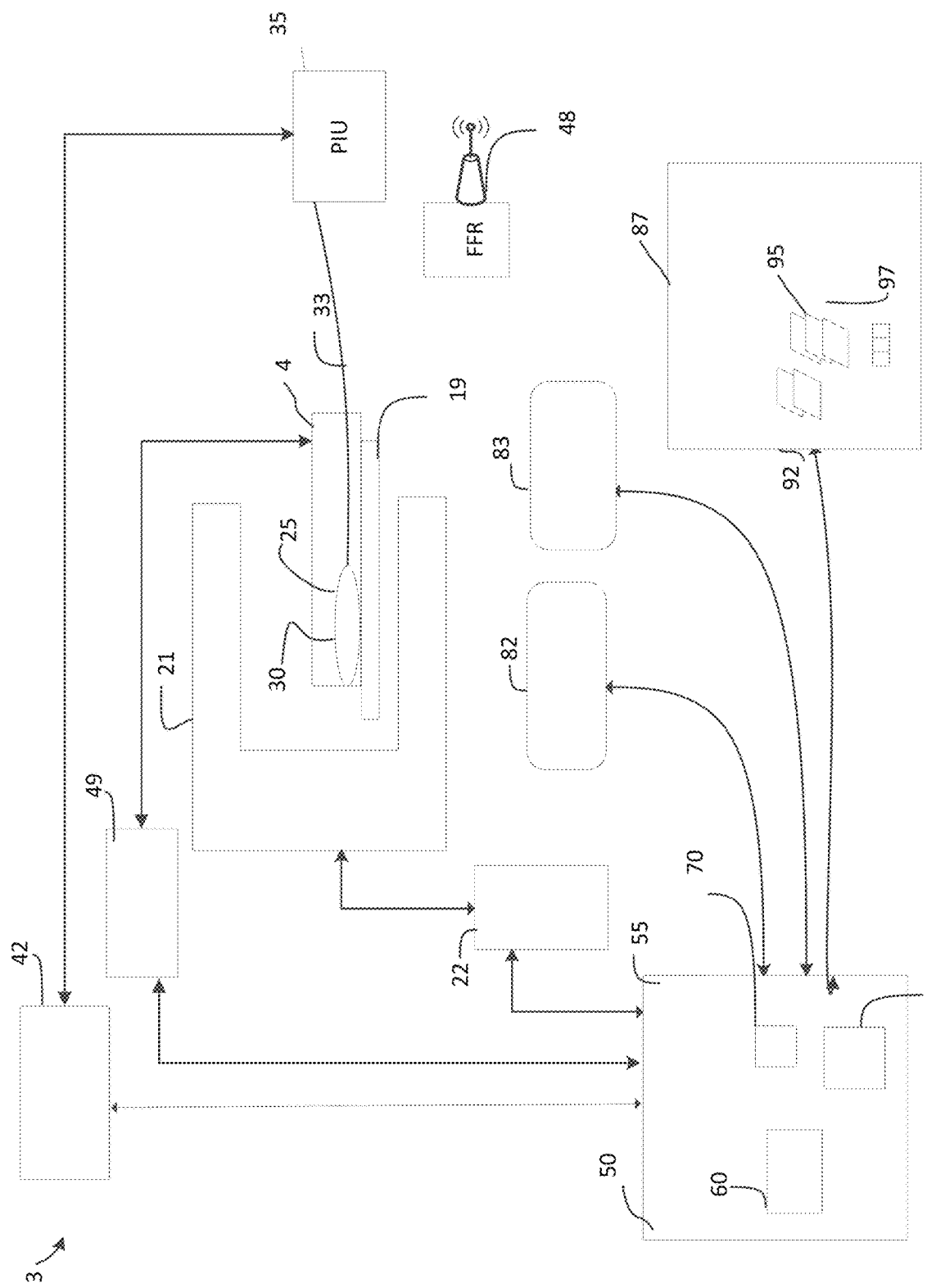
FIG. 1 shows a schematic, diagram of an intravascular imaging and data collection system in accordance with an illustrative embodiment of the disclosure.

In part, the disclosure relates to intravascular data collection systems, such as OCT, IVUS, and angiography systems and the exchange of data between two or more of the foregoing, as examples, and the generation and display of diagnostic information such as indicators. In one embodiment, intravascular data such as OCT is collected while angiography data is simultaneously collected. Indicators can include one or more one or two dimensional graphic elements and one or more associated indicia such as color, gray scale or other scale gradations, hashes, symbols or other visual elements.

One or more indicators can be generated and displayed such as by overlaying or otherwise combining such indicators with images generated using an intravascular data collection system. The indicators can include longitudinal, cross-sectional, and other indictor types such as one or more indicia or graphical elements suitable for indicating diagnostic information of interest such as tracking relative to user selected landmarks. Stent strut indicators can also be used. Methods of stent and shadow detection are described herein that can be used to display such intravascular features in a user interface and to display overlays relative thereto such as indicators or indicia. Angiography data can also be integrated and displayed with various common indicators as part of a co-registered display. In one embodiment, shadows and other dements which can be misconstrued as dissections, side branches or other vessel features can be shaded or otherwise changed to distinguish them and facilitate user review and analysis of images frames and data according to one embodiment.

Suitable diagnostic information can include stent apposition information such as the malapposition of a stent relative to a vessel wall or lumen boundary, user selected OCT positions in a vessel and associated angiography frame locations, and other intravascular diagnostic information or other information generated to facilitate stent delivery planning. The system includes a processor in communication with the graphical user interface and configured to send commands to the graphical user interface. One or more software programs are used to perform one or more of the following: co-register data such as frames of image data, generate and display longitudinal indicators indicative of stent position relative to a determined lumen boundary, code or mark data missing regions for an end user, translate user selected OCT position information to an angiography display using one or more graphical elements to facilitate co-registration, and visually identifying stents and simulated stents for planning purposes and others as described herein.

In part, the disclosure relates to a graphical user interface (GUI) element or indicator that is represented on a display relative to subject data such as image data or other intravascular parameters measured relative to the subject. Any clinically useful parameter as it changes longitudinally or cross-sectionally during the course of an Optical Coherence Tomography pullback recording or IVUS or other intravascular angiography system can be evaluated and displayed as an indicator or indicia. Each indicator/indicia can be used by interventional cardiologists to quickly see clinically useful information for an entire pullback recording in a single view without needing to manually manipulate the image. The indicator can guide a user to the particular points of interest in the vessel based on the parameter exceeding or falling below a clinically meaningful threshold value. By encoding the parameter value in a continuous color map, or other scale using suitable indicia for example, varying degrees of severity of the parameter can be easily summarized for the entire vessel in one easy to interpret view. These features are shown with the various apposition bars, stent indicators, and other indicators for angiography images and other intravascular data collection images.

Figure 2A:
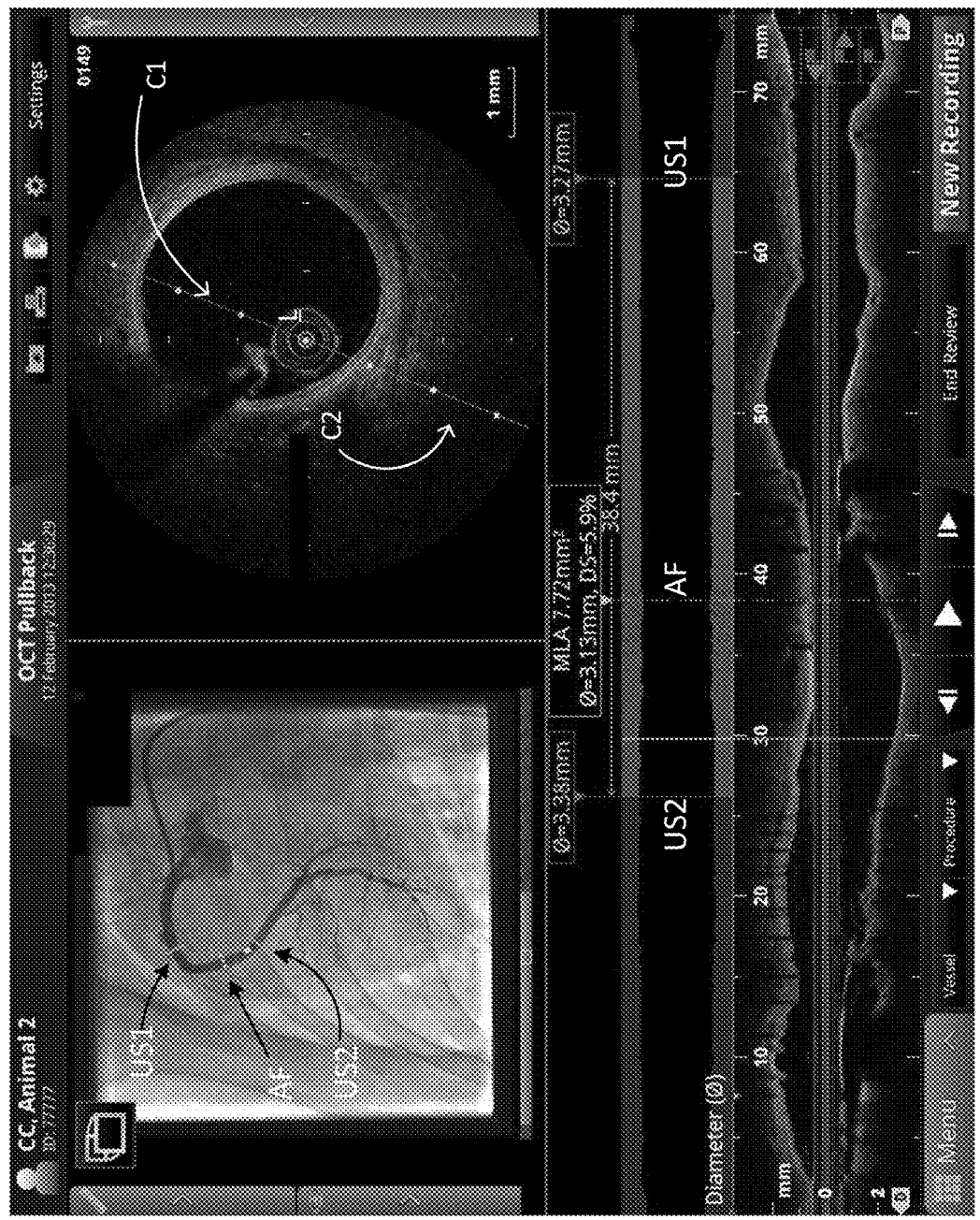
FIGS. 2A-2E show additional details relating to user interface displays and intravascular data, collection systems and indicators suitable therewith and angiography systems for diagnostic processes including stent delivery planning in accordance with an illustrative embodiment of the disclosure.
Figure 2B:
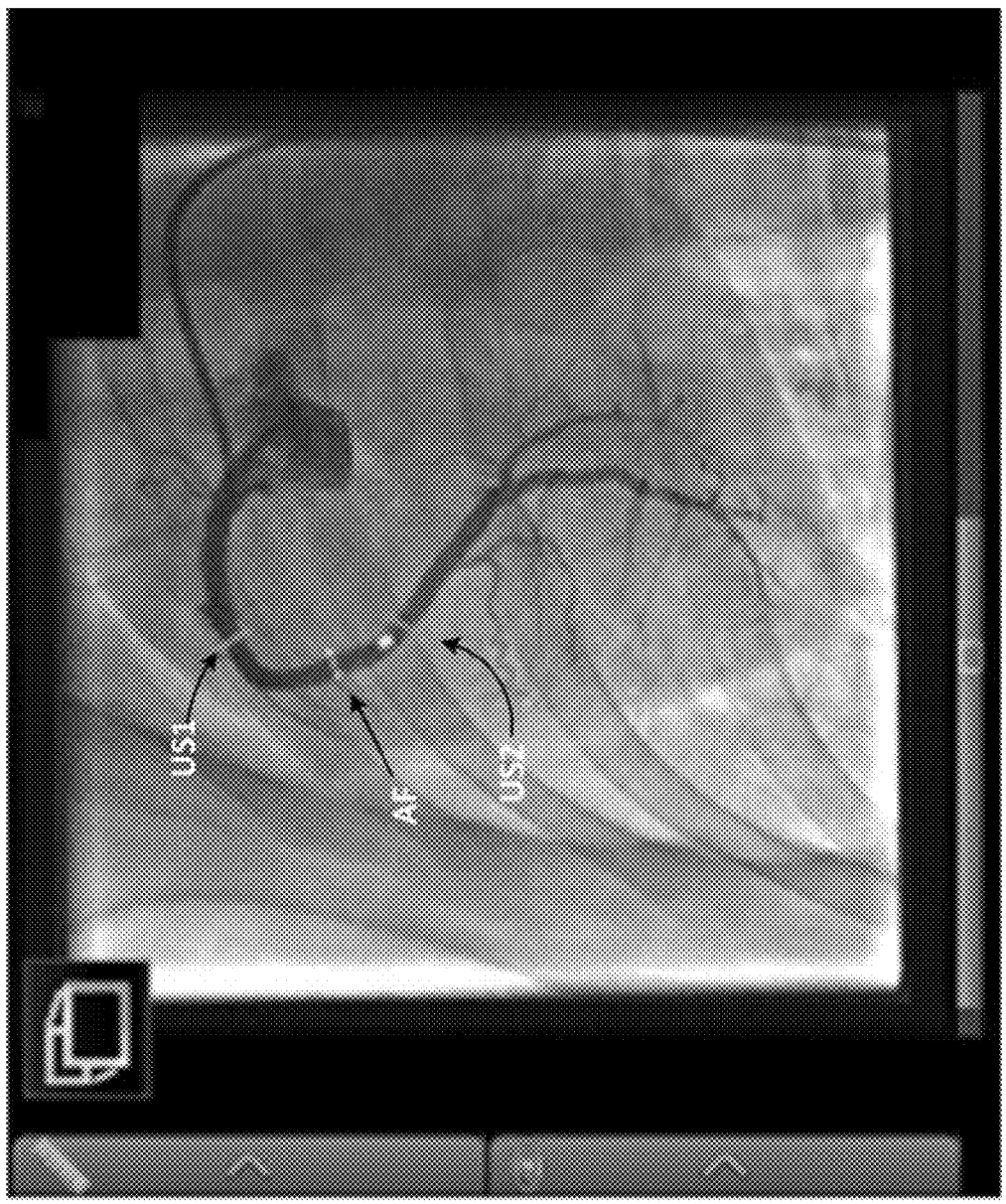
Figure 2C:
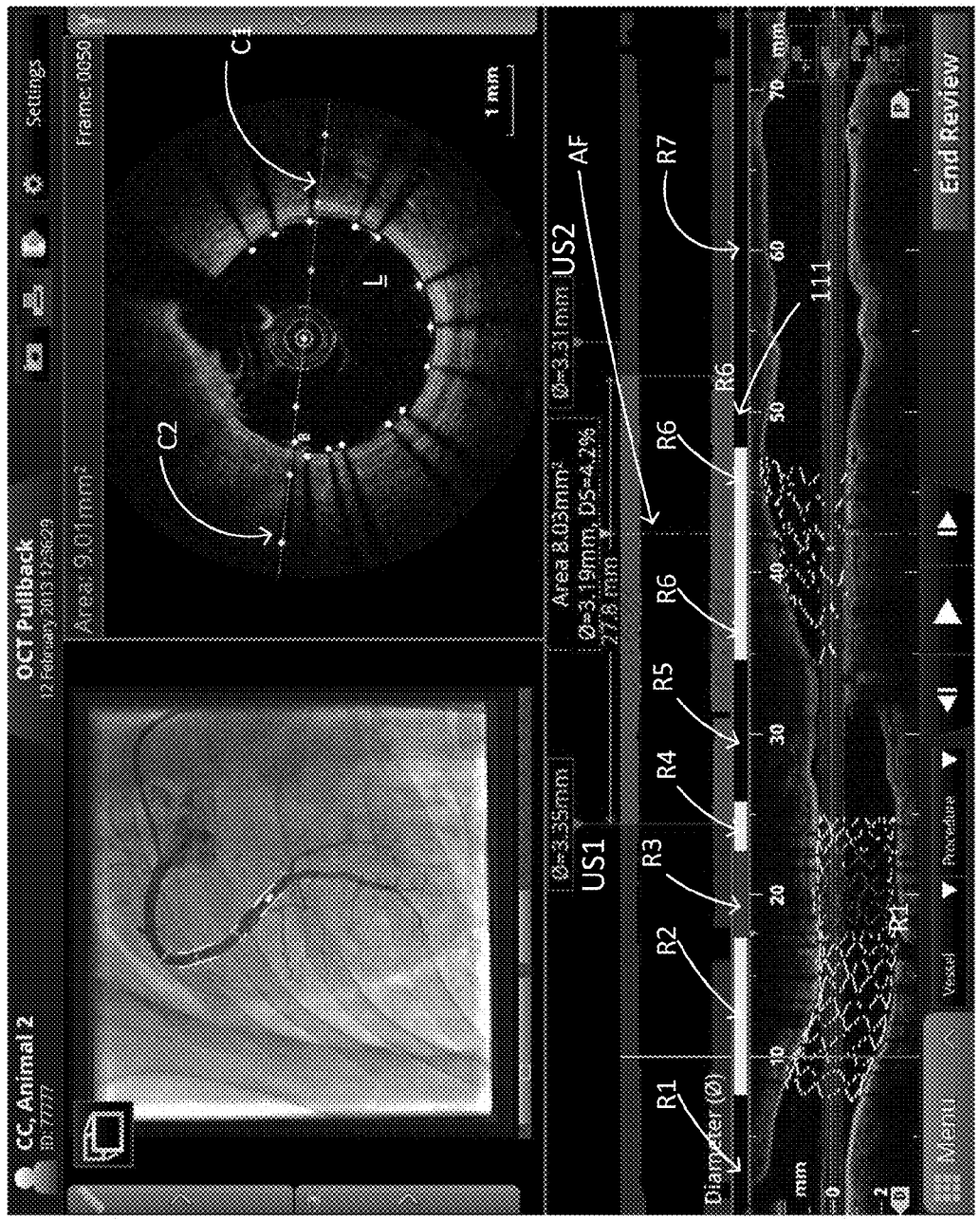

FIG. 1 includes a system suitable for performing sonic of these features. FIG. 2A shows four panels with the top tight panel including an angiography display with various indicators including a first user selected position US1, a second user selected position US2, and an active frame AF. These indicators are also shown in the bottom U-mode or longitudinal panel with US1 and US2 corresponding to the vertical lines shown and the active frame AF corresponding to the vertical line in between them. The active frame is shown in cross-sectional view at the top right panel. The middle panel shows the values of the US1 and US2 positions in ram as vessel positions and a calculated MLA. FIG. 2B shows a zoomed view of the angiography image of FIG. 1 which is co-registered with the OCT data of FIG. 1. These user interfaces include moveable elements C1, C2 that can be controlled by a user with a mouse, joystick, or other control and can be operated using one or more processors and memory storage elements. The movable elements C1, C2 are controls and can be rotated or moved as part of the interface. They are also shown in FIGS. 2C and 3B and others. In FIG. 3B, the controls C1, C2 are also represented as half circles relative to the stent struts and as line segments in the right panel.

Figure 2D:
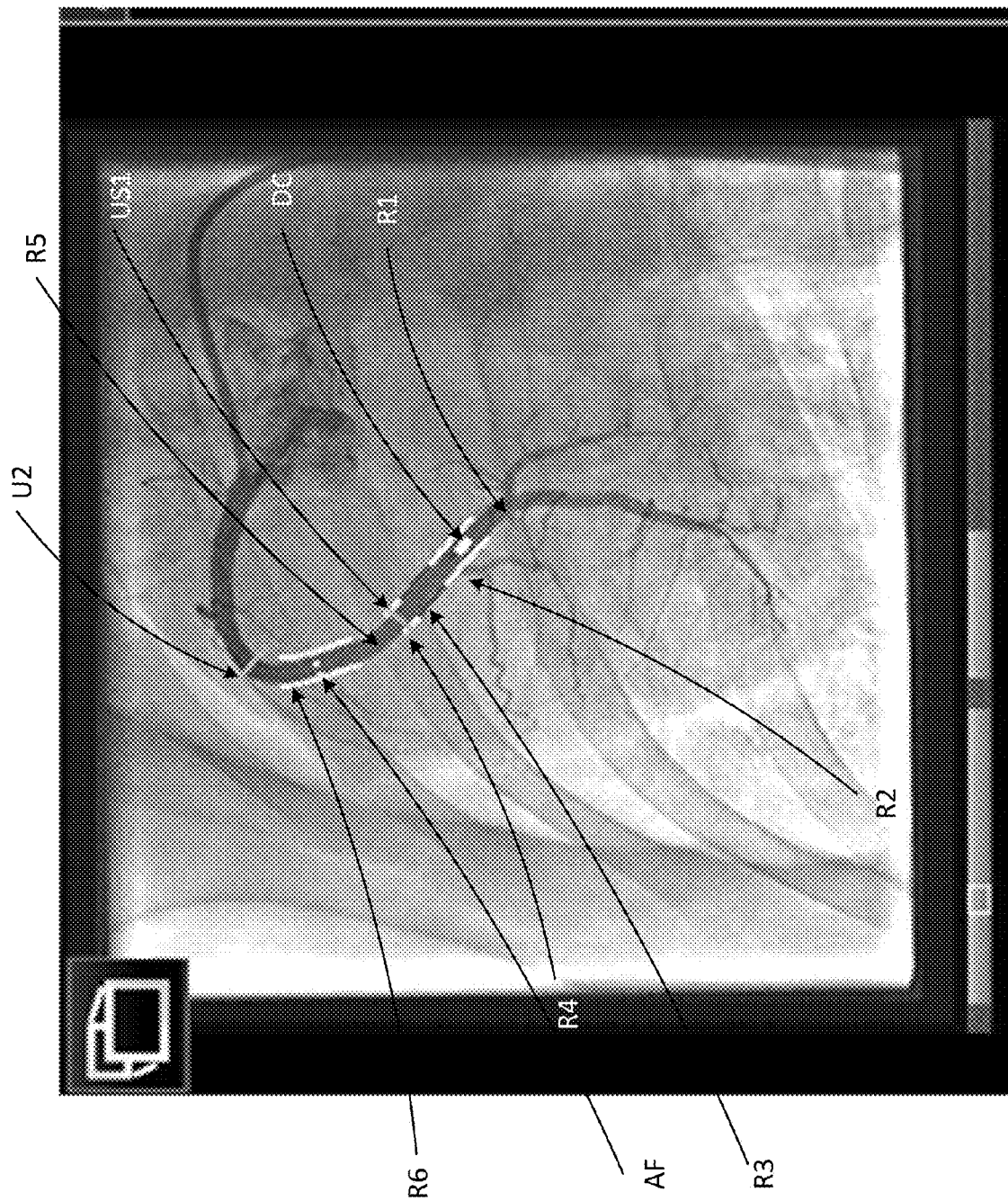
Figure 2E:
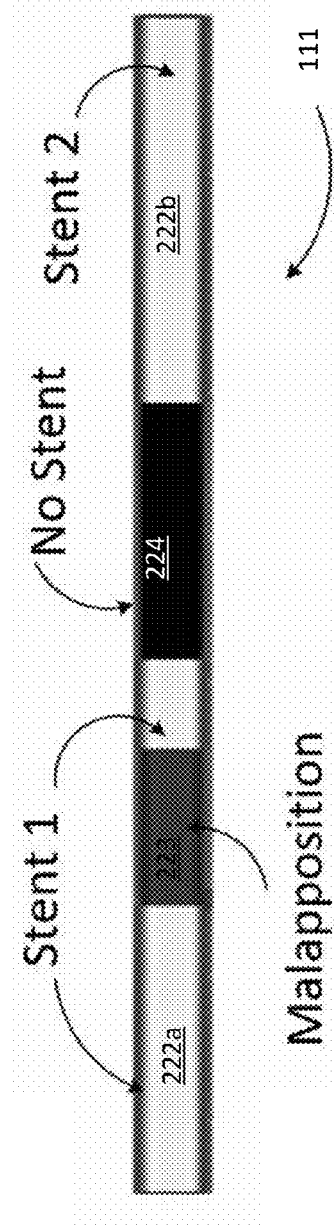

FIG. 2C shows an apposition bar/indicator bar 111 as an indicator with regions R1 to R7 which are shown in the angiography view in the top right which is shown in further detail in FIG. 2D. The top right panel shows R3 shows an area of apposition that is beyond a threshold of interest. In the L-mode, the stent struts are coded with an indicia such as symbols or color. The regions of apposition of interest in the apposition bar remain on display even if the dataset is rotated in order to bring the important areas to the attention of a user for stent planning and patient diagnosis. In this sense, indicators can be persistent to direct a user's focus during a planning or other procedure. FIG. 2E shows additional details relating to an exemplary apposition bar or indicator bar 111. The indicator bar 111 can be used for stent planning and review and to indicate regions in an intravascular image where there is apposition or another metric relative to a stent strut. The indicator bar 111 is persistent in the user interface views in one embodiment to alert a user to a stent region even if it is not visible based on the view selected by the user three-dimensional, cross-sectional, longitudinal, viewing angle, etc.

With regard to FIG. 2C, the two user selected points of interest are shown as U1 and U2. R3 corresponds to a region of malapposition of interest. R2 corresponds to a first stent and R6 corresponds to a second stent. R5 is the gap in between them. This data is co-registered with angiography data as shown in FIG. 2D to facilitate stent planning. Data collecting element of probe DC is shown in the image. R1 and R7 are distal and proximal areas in which no stent is present and correspond to vessel lumen. U1 and U2 serve as user placed landmarks that can be used by a user looking at live angio to give them a reference frame for the vessel section they marked with U1 and U2. One or more displays can be used such as live angio and OCT pullback data with previously acquired pullback frames.

With these and other indicators, the images and indicators can help as a tool to guide stent delivery based on the data shown in FIGS. 2C and 2D. The indicators can also show when a stent needs to be inflated in more detail given color coded or otherwise coded stent strut indicia in a cross-sectional or longitudinal view. In FIG. 2F, regions of a first stent 222a and a second stent 222b are shown by the apposition bar 111. A region of lumen or no stent 224 and malapposition region 223 are also shown. This bar 111 can be displayed on any angiography or OCT or IVUS image of interest. In one embodiment, an apposition bar is displayed such that it is intravascular view independent or persistent such that the apposition bar is displayed when no indicator or stent containing image is present. The various indicators and indicia can be generated based upon stent detection, lumen detection, stent apposition measurements and various graphic overlays generated using the system of FIGS. 1 and 10A, for example.

Figure 3A:
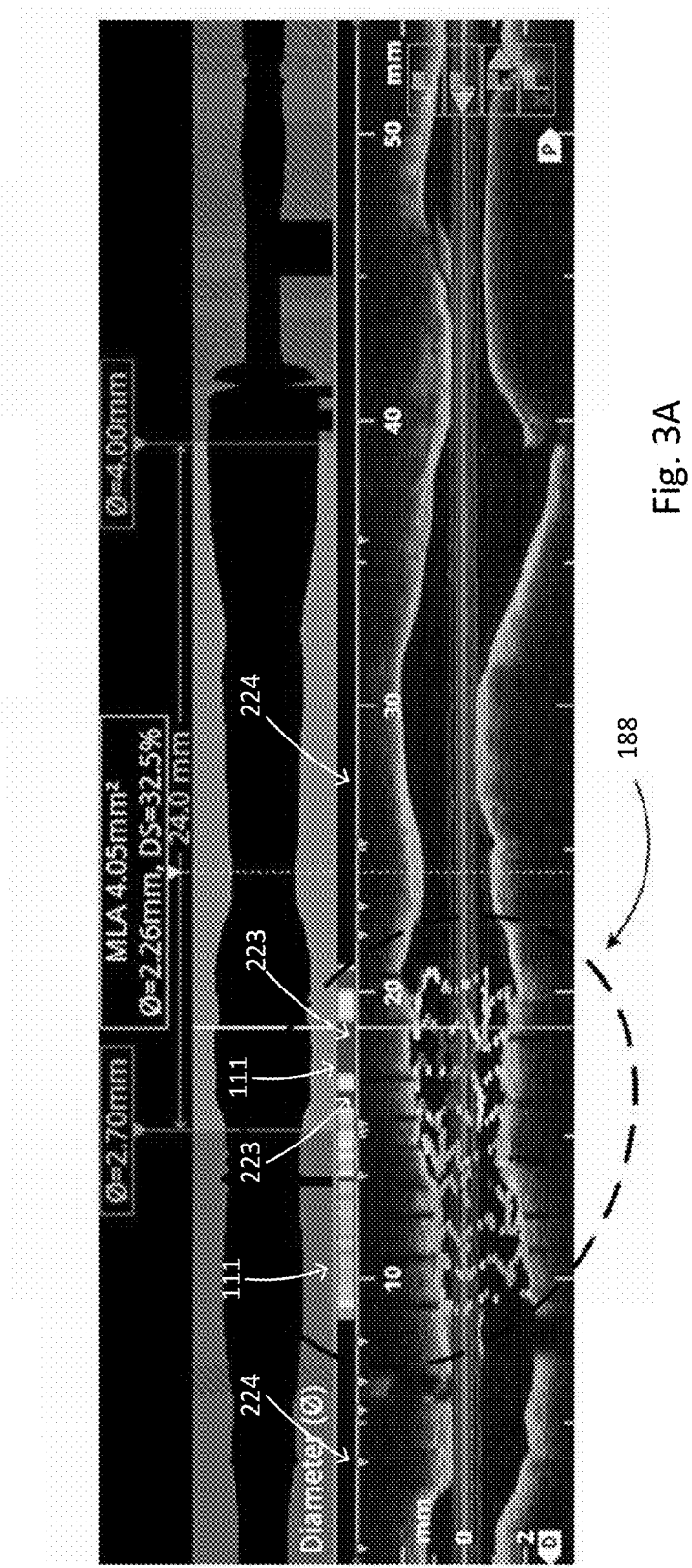
FIGS. 3A-6 show various user interfaces and data representations including various indicia and co-registered features relative to one or more imaging modalities in accordance with an illustrative embodiment of the disclosure.
Figure 3B:
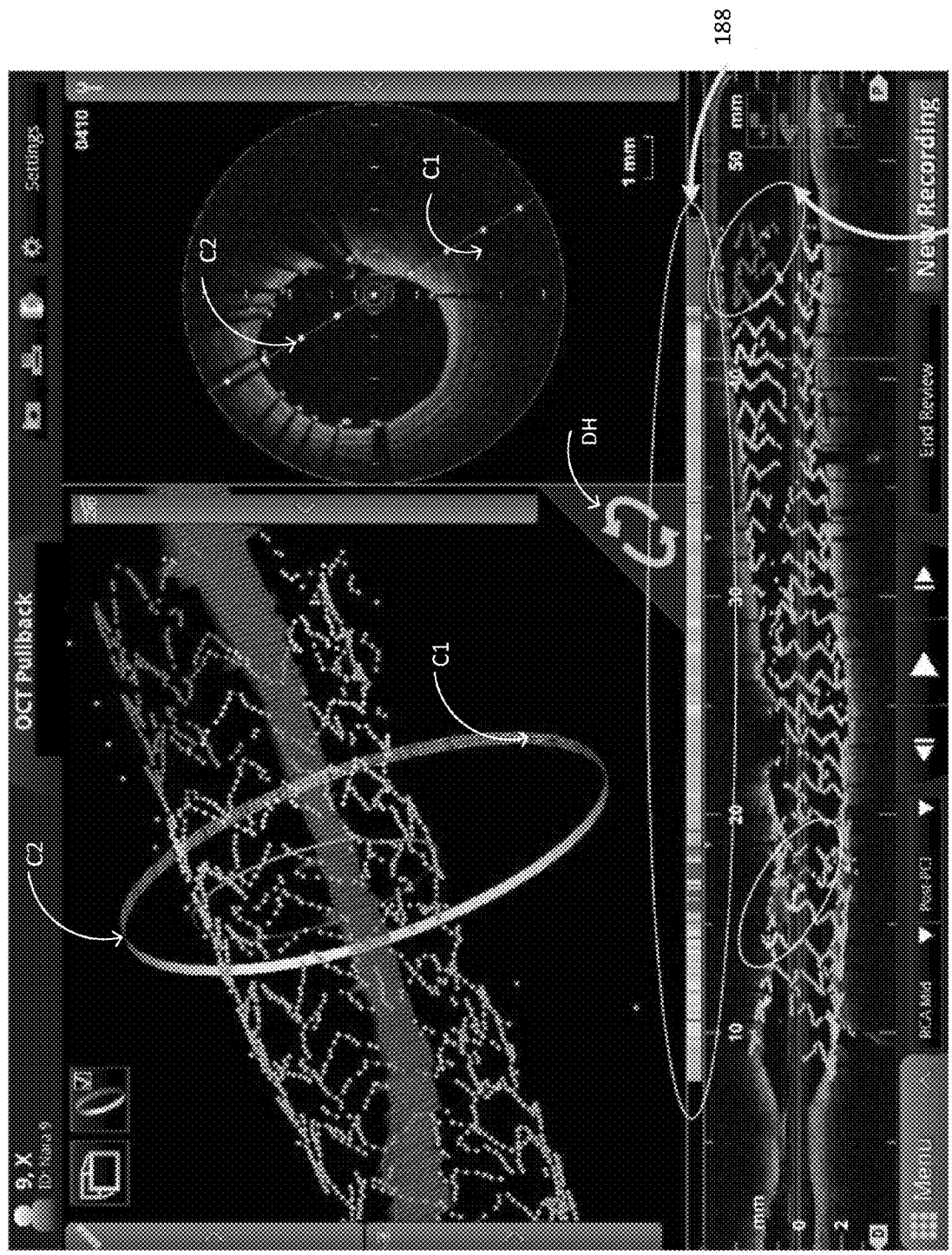

FIG. 3A shows an interface with a longitudinal view or L-mode showing an apposition bar above stent strut indicators coded based on apposition thresholds. The indicator bar 111 is shown in the middle of the GUI with no stent 224 regions and malapposition regions 223 shown. Lumen boundary data from OCT or IVUS is used to determine apposition issues such as thresholds being exceeded given detected strut data as inputs to the apposition bar generation software module. In FIG. 3B, the interface screen depicts an example of the indicator measuring a high level of apposition for a metallic stent strut as shown above the L-Mode display in the GUI screen shot shown. The apposition indicator allows for the summary information about the clinical parameter to be displayed without the need to manually manipulate or inspect the image data. A stent apposition bar and other indicators shown herein and their co-registration with angiography offer many advantages to a user.

Figure 4A:
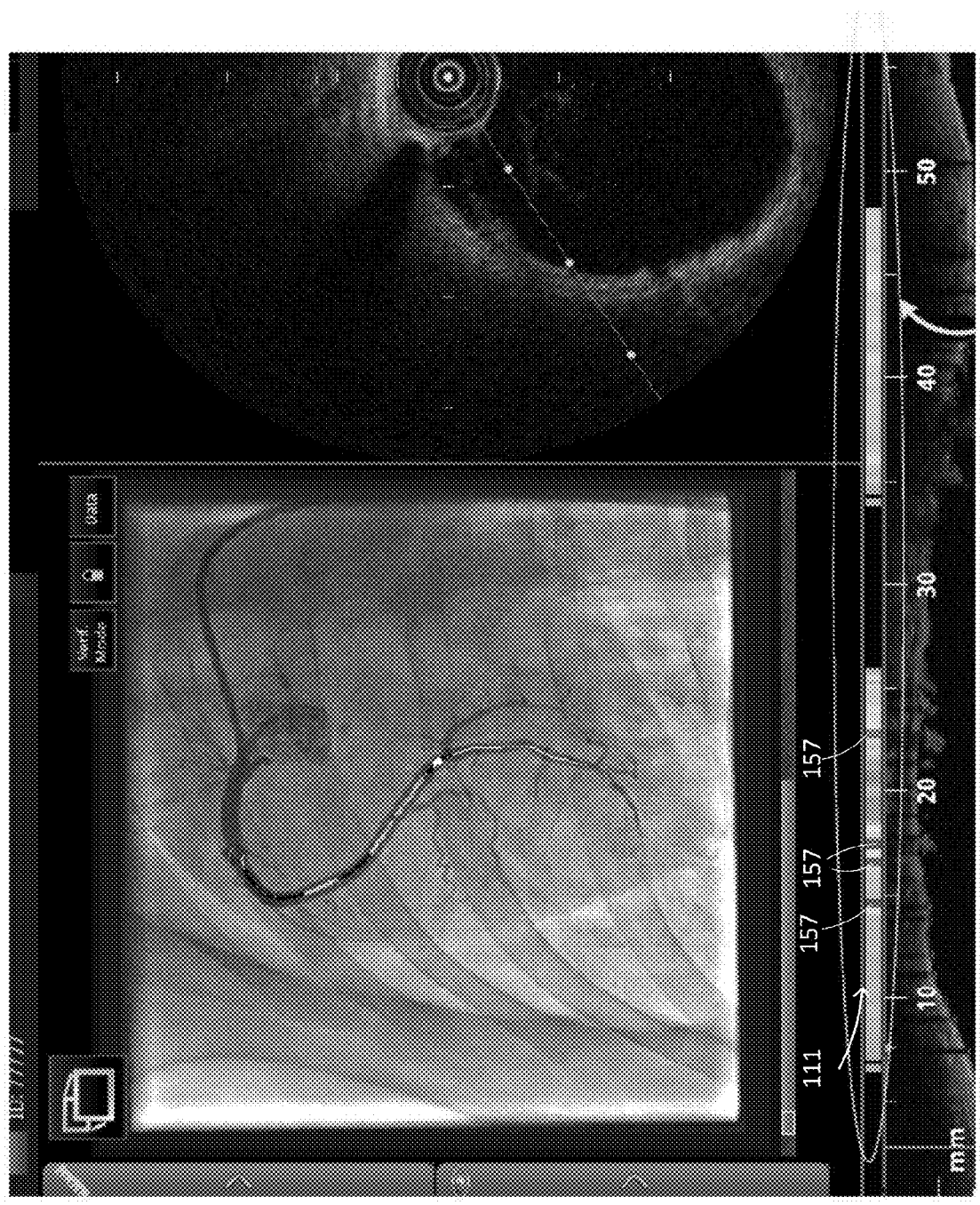
Figure 4B:

In FIGS. 3A, 3B, 4A, and 4B some embodiments of user interfaces depicting intravascular data and angiography data (where applicable) along with an exemplary indicator for stent strut apposition and other indicator-based data displays. In one embodiment, the apposition bar is shown on L-Mode and angiography images, three-dimensional flow through images and others. FIG. 4B shows an angiography image with stent data showing threshold information along the outer boundary of the vessel as well as a longitudinal view of the apposition bar 111. A region 161a in the angiography portion of the user interface is also aligned with a region 161b of the indicator bar 111. In one embodiment, the angiography images are aligned or registered with the apposition bar. One feature of the apposition bar 111 is that it is persistent in the user interfaces such that if a stent is present in a 2 or 3D image, but it does not appear based on the cut plane or viewing angle, the apposition bar would persist and show that a stent and any associated malapposition is present even though a 2D or 3D stent does not appear in the GUI. This is a useful feature for stent planning an diagnostics.

In FIG. 4A, an indicator bar 111 is shown that indicates stent struts and apposition areas of interest 157. These areas of interest 157 showing apposition can be grouped with a representation of the stent struts themselves and color coded or coded with another indicia that is viewable in a GUI. An example of a grouping of stent struts code with air indicia and the indicator bar is shown by region 188 in FIGS. 3A, 3B, 5 and 6. In these regions 188, an indicator bar 111 is shown aligned with a representation of a stent and a series of struts with various indicia corresponding to apposition relative to the vessel wall. A detected lumen boundary is used to compare stent position relative thereto. Additional details relating to stent detection are included herein.

Figure 5:
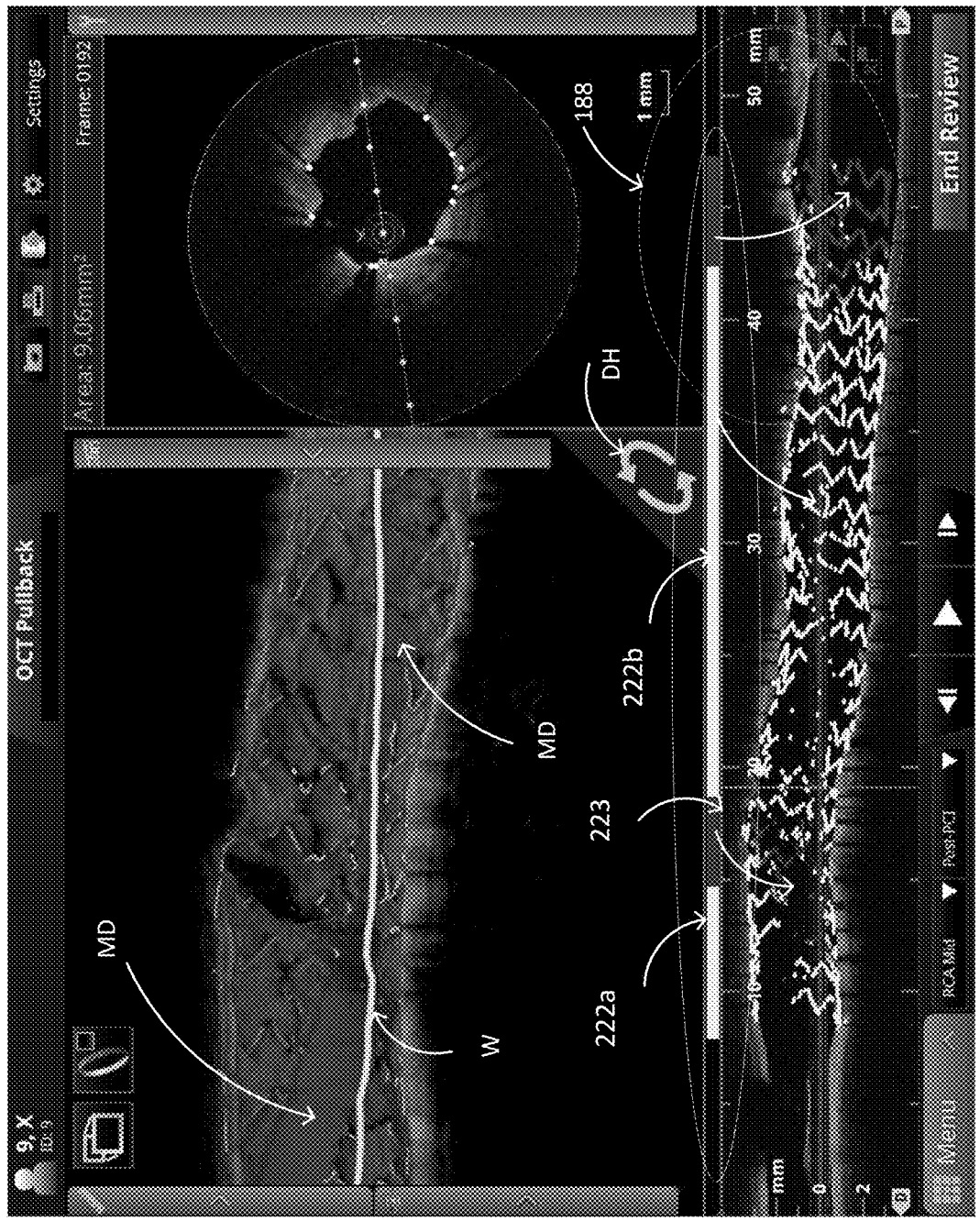

FIG. 5 shows another GUI with an indicator or image data processing feature by which missing data such as data obscured or missing the shadow of a guidewire is modified by software to replace it with a gray mask or another indicator. To avoid user confusion with side branches, dissections, or missing data an indicator MD is used to indicate regions where data is missing. This has the benefit of preventing a user from mistaking it for missing data, a dissection area, or a side branch. In one embodiment, areas where data is missing as a result of a shadow or otherwise are displayed with an indicia or indicator such as a gray region, a colored region, hashing, or another visible indicia. The double headed arrow icon in the middle allows the view to be rotated. This user control along with the apposition bar and identification of a guidewire by color coding or other indicia all improve and extend the diagnostic range of the image data from an intravascular data collection probe and/or angiography data.

Figure 6:
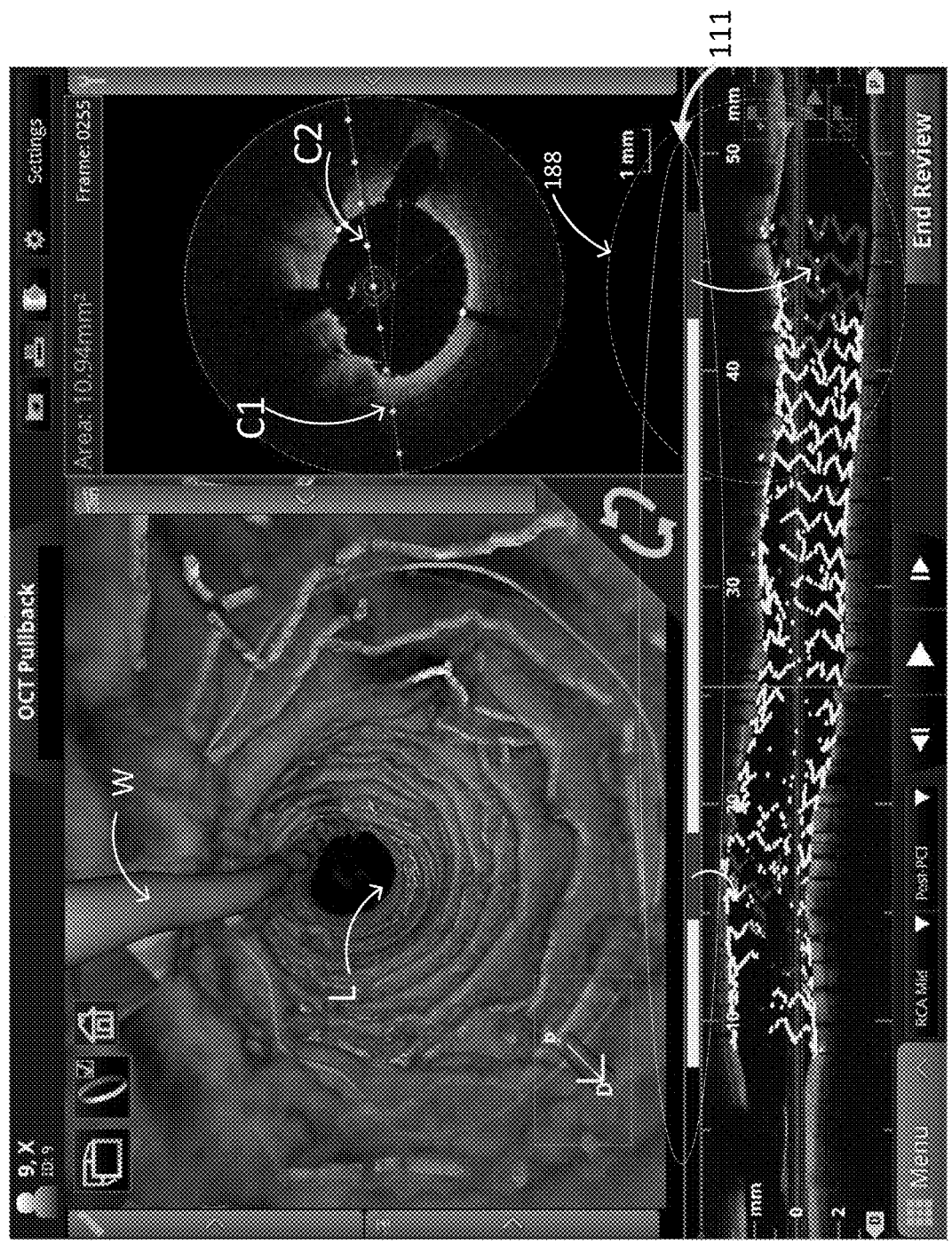

In another embodiment, as shown in FIG. 5. an indicator W is used to point to a guidewire image. In one embodiment, the indicator W can be used to identify a guidewire in the GUI or select it for removal from image. FIG. 6 shows a three-dimensional fly though with the apposition bar shown as a trajectory ahead of the viewing plane of the user corresponding to the cross-section on the right. Indicator bar 111 showing stent struts and apposition areas of interest— included in 3D fly thought view and any other view of interest—regions of interest remain viewable during rotation to alert user of important vessel regions during stent planning.

Figure 7A:
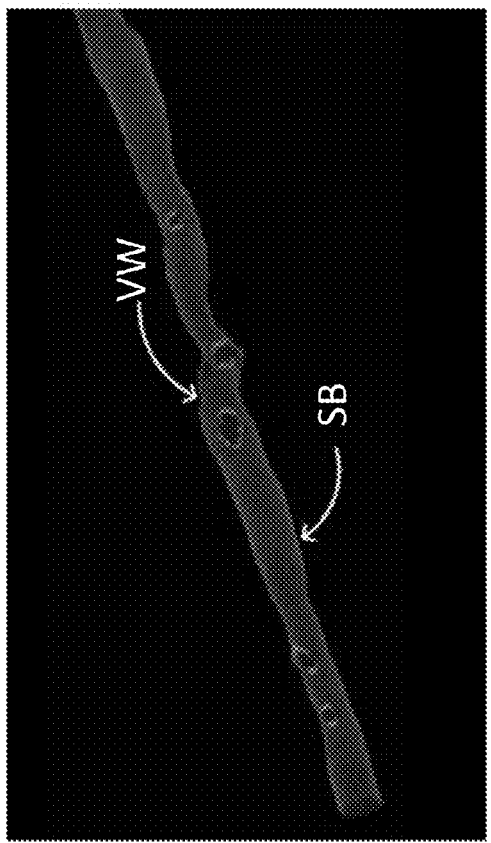
FIGS. 7-7B show a three-dimensional representation of side branch indicators generated using intravascular imaging data such as OCT data in accordance with an illustrative embodiment of the disclosure.
Figure 7B:
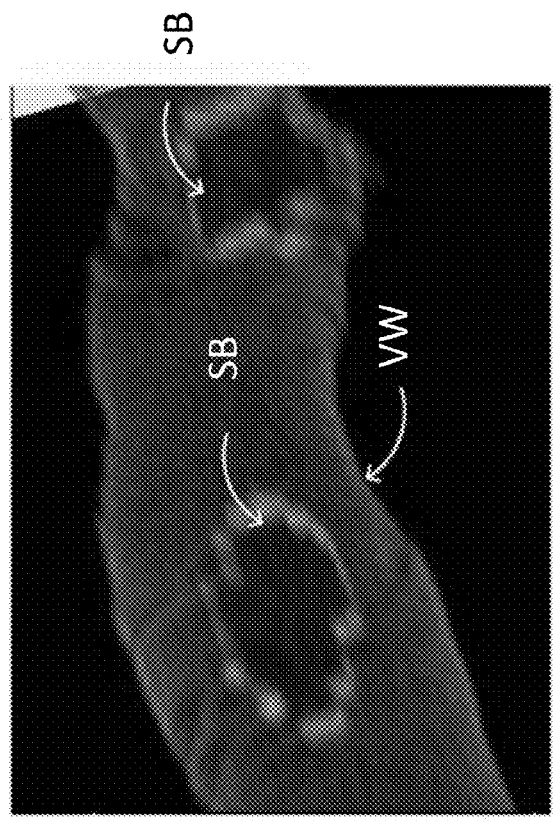
Figure 8A:
FIGS. 8A-9B show additional details relating to user interface displays and intravascular data collection systems and indicators suitable therewith and angiography systems for diagnostic processes.
Figure 8B:
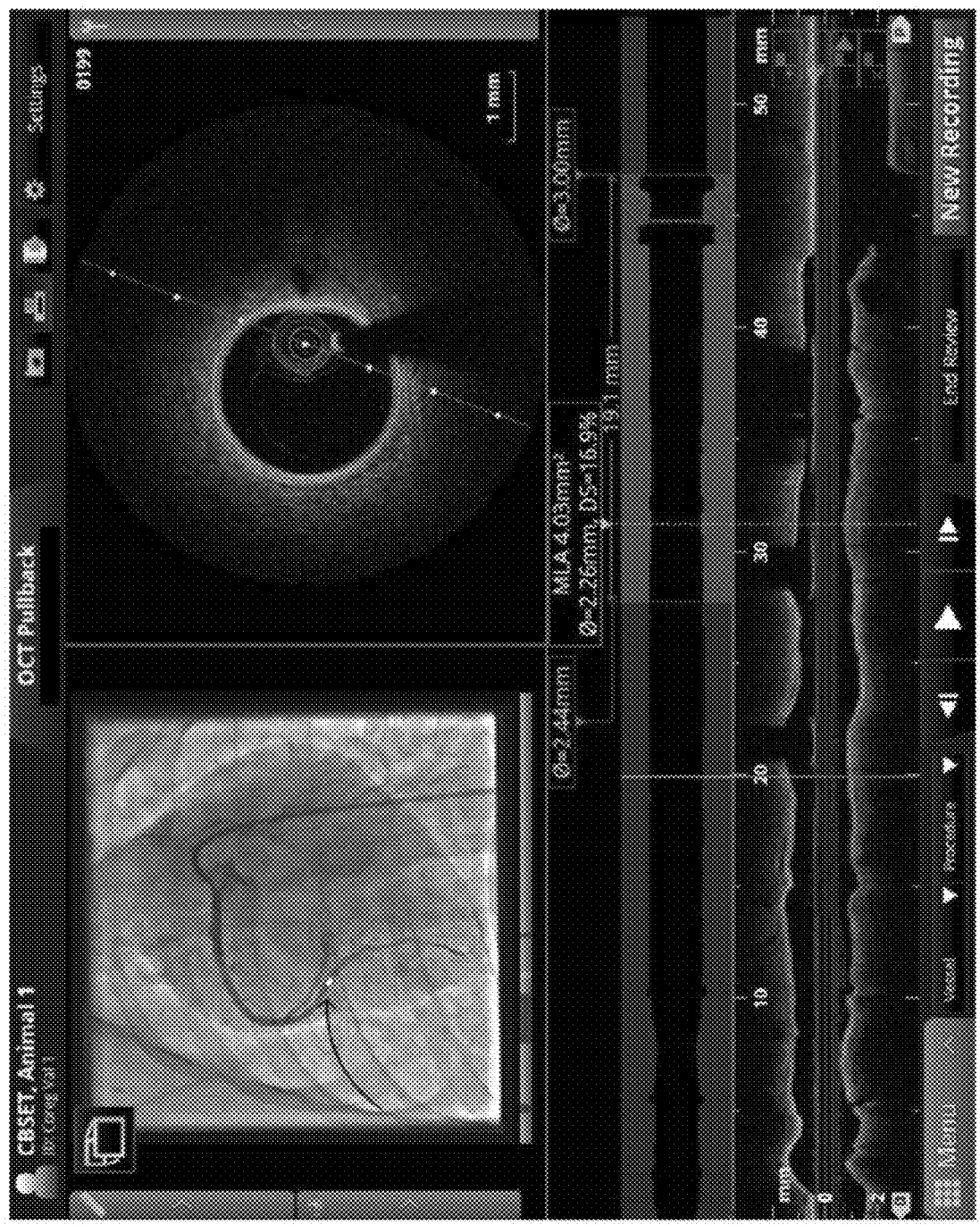
Figure 9A:
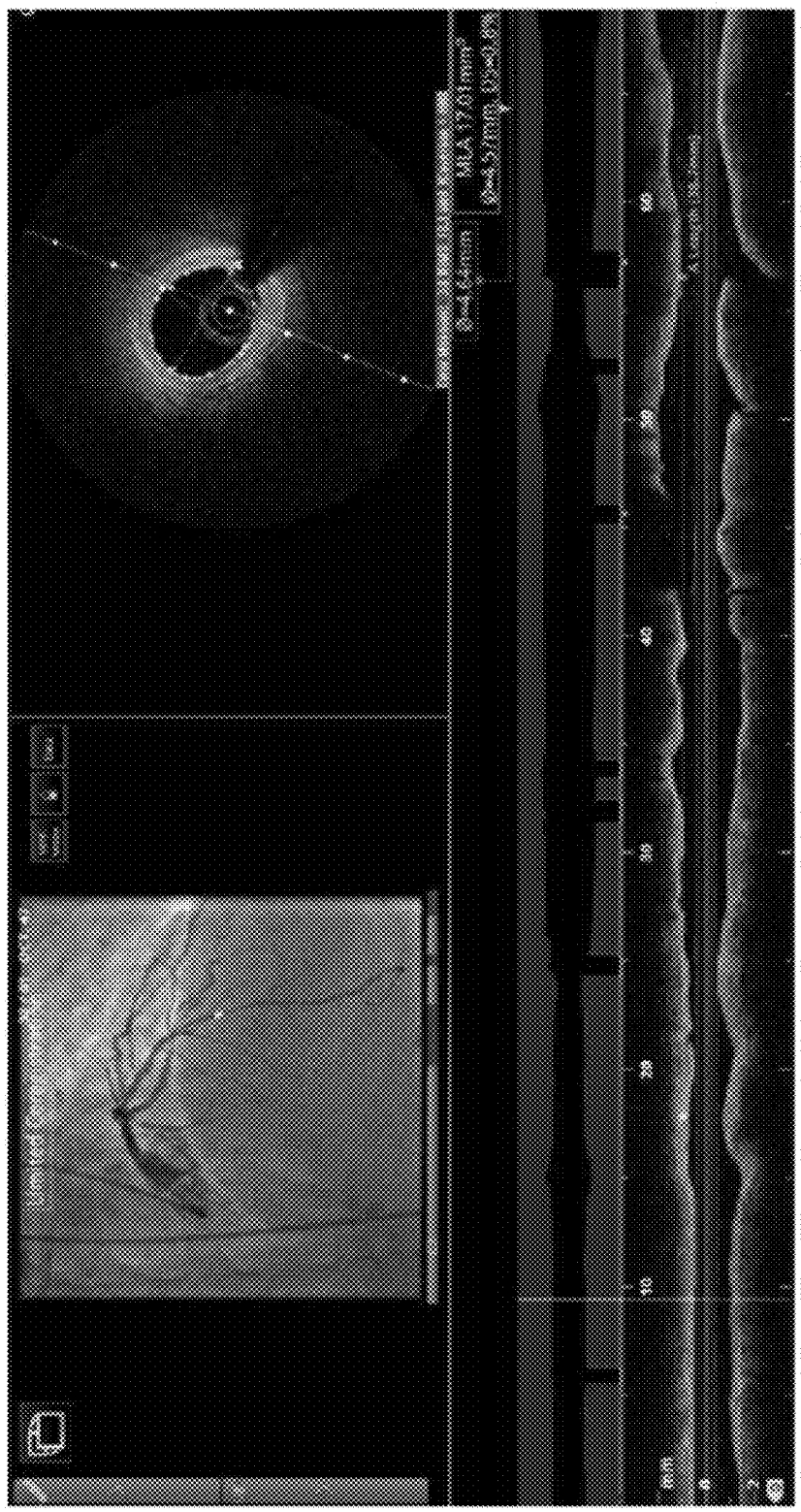
Figure 9B:
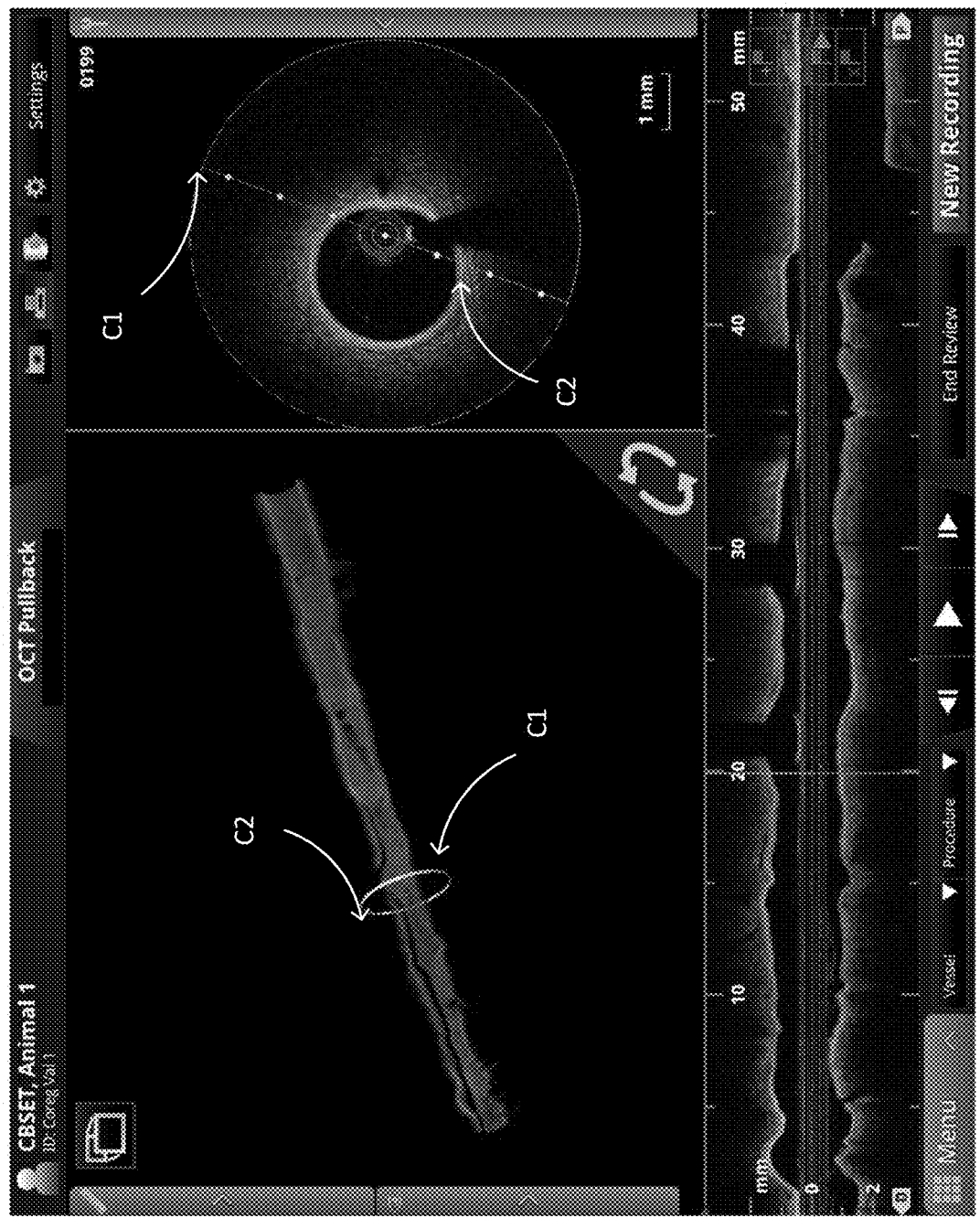

FIGS. 7A and 7B show other indicators SB corresponding to side branches. A rendering of the vessel wall VW is also shown relative to the side branches. These and other indicators can be used to emphasize regions in 2D and 3D data. As shown in the user interfaces depicted, such as FIG. 9B, the various circles/line segments C1, C2 in the top right view can be rotated to navigate through various views of the image. FIGS. 8A to 9B show additional interfaces and control information for navigating image data sets and performing diagnostics such as stent planning. Various proximal and distal views and other perspective views can be navigated using the tools shown herein. In one or more embodiments, the indicators such as apposition bar 111 are persistent such that they remain in view even if navigated away from an area of malapposition.

Thus, some indicators are rotationally agnostic such that if the indicator includes a region or length that includes a parameter that exceeds a threshold then that region remains indicated as such even if the image data is changed such that the rotated view obscures the region such as a malapposed stent region. Thus, if one side of a vessel has an apposition issue, the user remains aware of it relative to their location in the vessel. The apposition bar can be displayed as an indicator in one or more views of an angiography or OCT image or user-interfaces.

As shown in the various figures, the apposition bar 111 can be subdivided into various regions or lengths indicative of the presence of or more stents in the vessel or the malposition or the gap in between stents for a multi-stented vessel. The angiography data and associate image frames can be co-registered with OCT data. Further, as shown in the figure user selected vertical lines corresponding certain longitudinal distances on the artery can be set to guide stent planning. The rotational agnostic or persistent nature of the bar provides further assistance and error reduction during stem planning.

During a stent delivery planning procedure, clinician specified landmarks can be used for stunt planning by providing a reference for a user to select stunt sizes and relative to the vessel with respect to which user can refer to while deploying a stent using live angio. Given the levels and location of malapposition the user can refer to OCT and annotated angiography to further expand or move a stent as part of delivery planning. These system features and methods can be implemented using system 3 shown in FIG. 1 and the system of FIG. 10A, for example.

FIG. 1 shows a system 3 which includes various data collection subsystems suitable for collecting data or detecting a feature of or sensing a condition of or otherwise diagnosing a subject 4. In one embodiment, the subject is disposed upon a suitable support 19 such as table bed to chair or other suitable support. Typically, the subject 4 is the human or another animal having a particular region of interest 25.

The data collection system 3 includes a noninvasive imaging system such as a nuclear magnetic resonance, x-ray, computer aided tomography, or other suitable noninvasive imaging technology. As shown as a non-limiting example of such a noninvasive imaging system, an angiography system 21 such as suitable for generating cines is shown. The angiography system 21 can include a fluoroscopy system. Angiography system 21 is configured to noninvasively image the subject 4 such that frames of angiography data, typically in the form of frames of image data, are generated while a pullback procedure is performed using a probe 30 such that a blood vessel in region 25 of subject 4 is imaged using angiography in one or more imaging technologies such as OCT or IVUS, for example.

The angiography system 21 is in communication with an angiography data storage and image management system 22, which can be implemented as a workstation or server in one embodiment. In one embodiment, the data processing relating to the collected angiography signal is performed directly on the detector of the angiography system 21. The images from system 21 are stored and managed by the angiography data storage and image management 22.

In one embodiment system server 50 or workstation 87 handle the functions of system 22. In one embodiment, the entire system 21 generates electromagnetic radiation, such as x-rays. The system 21 also receives such radiation after passing through the subject 4. In turn, the data processing system 22 uses the signals from the angiography system 21 to image one or more regions of the subject 4 including region 25. This system allows the angiography data to be shown on displays 82 and 82 along with intravascular data and the various indicators and detected stent struts and shadows as described herein.

As shown in this particular example, the region of interest 25 is a subset of the vascular or peripherally vascular system such as a particular blood vessel. This can be imaged using OCT, A catheter-based data collection probe 30 is introduced into the subject 4 and is disposed in the lumen of the particular blood vessel, such as for example, a coronary artery. The probe 30 can be a variety of types of data collection probes such as for example an OCT probe, an FFR probe, an IVUS probe, a probe combining features of two or more of the foregoing, and other probes suitable for imaging within a blood vessel. The probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For an intravascular probe that includes an optical beam director, the optical fiber 33 is in optical communication with the probe with the beam director. The torque wire defines a bore in which an optical fiber is disposed. In FIG. 1, the optical fiber 33 is shown without a torque wire surrounding it. In addition, the probe 30 also includes the sheath such as a polymer sheath (not shown) which forms part of a catheter. The optical fiber 33, which in the context of an OCT system is a portion of the sample arm of an interferometer, is optically coupled to a patient interface unit (PIU) 35 as shown.

The patient interface unit 35 includes a probe connector suitable to receive an end of the probe 30 and be optically coupled thereto. Typically, the data collection probes 30 are disposable. The PIU 35 includes suitable joints and elements based on the type of data collection probe being used. For example a combination OCT and IVUS data collection probe requires an OCT and IVUS PIU. The PIU 35 typically also includes a motor suitable for pulling back the torque wire, sheath, and optical fiber 33 disposed therein as part of the pullback procedure. In addition to being pulled back, the probe tip is also typically rotated by the PIU 35. In this way, a blood vessel of the subject 4 can be is longitudinally or via cross-sections. The probe 30 can also be used to measure a particular parameter such as an FFR or other pressure measurement. The image data can be used to generate various 2D and 3D views which can be navigated as shown in the user interface depictions.

In turn, the PIU 35 is connected to one or more intravascular data collection systems 42. The intravascular data collection system 42 can be an OCT system, an IVUS system, another imaging system, and combinations of the foregoing. For example, the system 42 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 42 can include ultrasound signal generating and processing circuitry, noise filters, rotatable joint, motors, and interface units. In one embodiment, the data collection system 42 and the angiography system 21 have a shared clock or other timing signals configured to synchronize angiography video frame time stamps and OCT image frame time stamps.

In addition to the invasive and noninvasive image data collection systems and devices of FIG. 1, various other types of data can be collected with regard to region 25 of the subject and other parameters of interest of the subject. For example, the data collection probe 30 can include one or more pressure sensors such as for example a pressure wire.

A pressure wire can be used without the additions of OCT or ultrasound components. Pressure readings can be obtained along the segments of a blood vessel in region 25 of the subject 4.

Such readings can be relayed either by a wired connection or via a wireless connection. As shown in a fractional flow reserve FFR data collection system, a wireless transceiver 48 is configured to receive pressure readings from the probe 30 and transmit them to a system to generate FFR measurements or more locations along the measured blood vessel. One or more displays 82, 83 can also be used to show an angiography frame of data, an OCT frame, user interfaces for OCT and angiography data, shadows, indicators, missing data and other controls and features of interest.

The intravascular image data such as the frames of intravascular data generated using the data collection probe 30 can be routed to the data collection processing system 42 coupled to the probe via PIU 35. The noninvasive image data generated using angiography system 22 can be transmitted to, stored in, and processed by one or more servers or workstations such as the co-registration server 50 workstation 87. A video frame grabber device 55 such as a computer board configured to capture the angiography image data from system 22 can be used in various embodiments.

In one embodiment, the server 50 includes one or more co-registration software modules 60 that are stored in memory 70 and are executed by processor 80. The server 50 can include other typical components for a processor-based computing server. Or more databases such as database 90 can be configured to receive image data generated, parameters of the subject, and other information generated, received by or transferred to the database 90 by one or more of the systems devices or components shown in FIG. 1. Although database 90 is shown connected to server 50 while being stored in memory at workstation 87 this is but one exemplary configuration. For example, the software modules 60 can be running on a processor at workstation 87 and the database 90 can be located in the memory of server 50. The device or system use to run various software modules are provided as examples. In various combinations the hardware and software described herein can be used to obtain frames of image data, process such image data, and rester such image data.

As otherwise noted herein, the software modules 60 can include software such as preprocessing software, transforms, matrices, lumen detection, stent detection, shadow detection, indicator generator and display, and other software-based components that are used to process image data or respond to patient triggers to facilitate co-registration of different types of image data by other software-based components 60 or to otherwise perform such co-registration. The modules can include lumen detection using a scan line based or image based approach, stent detection using a scan line based or image based approach, indicator generation, apposition bar generation for stent planning, guidewire shadow indicator to prevent confusion with dissention, side branches and missing data, and others.

The database 90 can be configured to receive and store angiography image data 92 such as image data generated by angiography system 21 and obtained by the frame grabber 55 server 50. The database 90 can be configured to receive and store OCT image data 95 such as image data generated by OCT system 42 and obtained by the frame gabber 55 server 50.

In addition, the subject 4 can be electrically coupled via one or more electrodes to one more monitors such as, for example, monitor 49. Monitor 49 can include without limitation an electrocardiogram monitor configured to generate data relating to cardiac function and showing various states of the subject such as systole and diastole. Knowing the cardiac phase can be used to assist the tracking of vessel centerlines, as the geometry of the heart, including the coronary arteries, is approximately the same at a certain cardiac phase, even over different cardiac cycles.

Hence, if the angiography data spans a few cardiac cycles, a first-order matching of vessel centerline at the same cardiac phase may assist in tracking the centerlines throughout the pullback. In addition, as most of the motion of the heart occurs during the systole, vessel motion is expected to be higher around the systole, and damp towards the diastole. This provides data to one or more software modules as an indication of the amount of motion expected between consecutive angiography frames. Knowledge of the expected motion can be used by one or more software modules to improve the tracking quality and vessel centerline quality by allowing adaptive constraints based on the expected motion.

Shadow Detection Related Embodiments

The disclosure provides, in part, methods and systems for identifying within a detected stent shadow the precise offset, or location, of the strut resulting in the detected shadow. Sometimes, within a shadow there is a single possible strut location corresponding to a bright strut bloom, or peak, against a dark shadow background in the scan line. However, multiple strut peaks often are detected inside a strut shadow, making it difficult to identify the exact location of a stent strut. Spurious peaks can be caused by, for example, blood pooling, poor blood clearing in the pullback zone, or ringing artifacts due to the imaging optics interacting with the metal strut. The present disclosure provides methods and systems for identifying the best candidate for a true stent within a stent shadow.

Figure 10A:
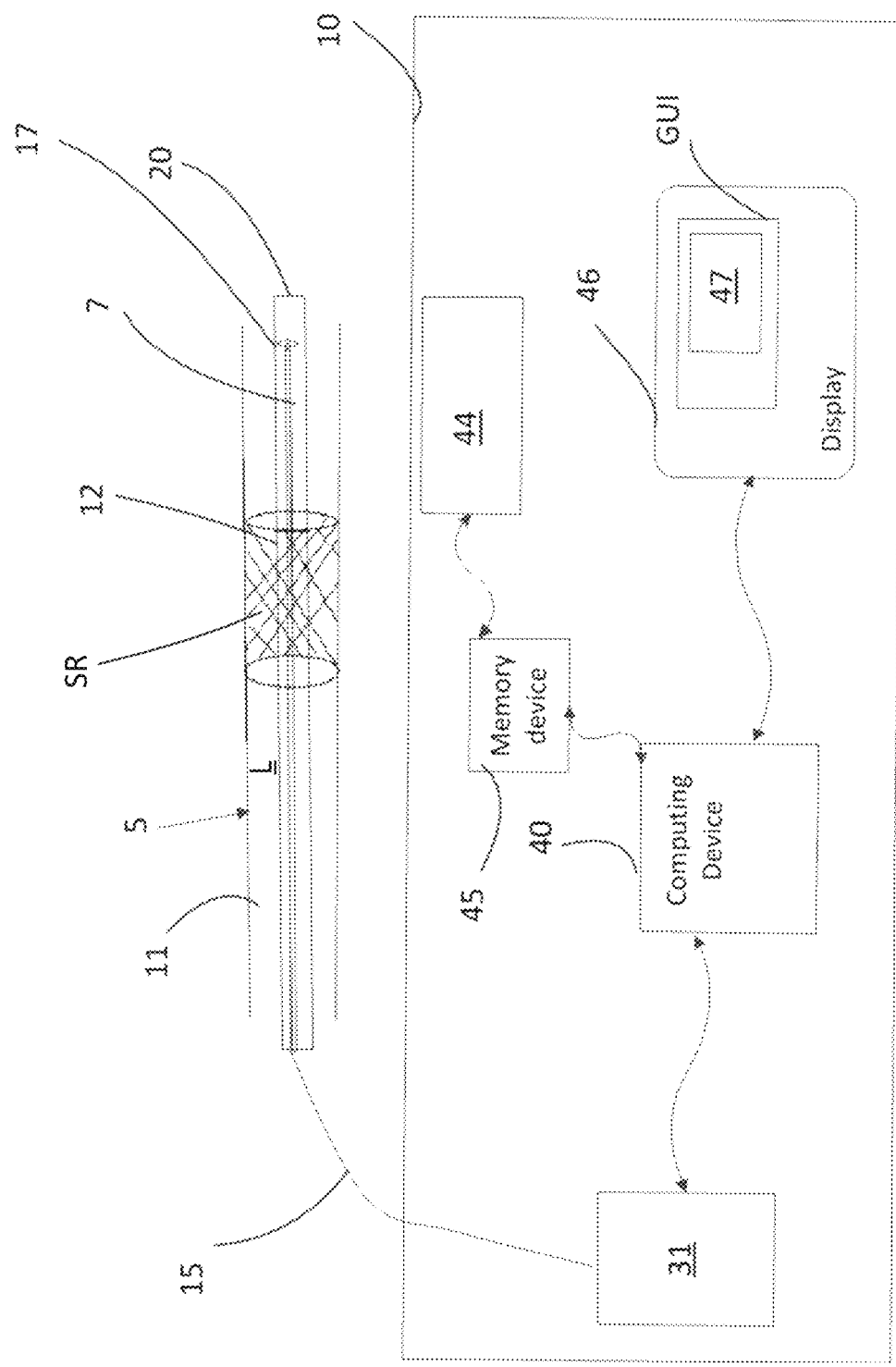
FIG. 10A is an exemplary intravascular data collection system and an associated intravascular data collection probe and related image processing, detection, and other software components according to an illustrative embodiment of the disclosure.

FIG. 10A is a high level schematic diagram depicting a blood vessel 5, such as an artery, a data collection probe 7 and an intravascular data collection and processing system 10. The methods described with regard to system 10 of FIG. 10A can also be performed with system 3 of FIG. 1 and other systems. In particular, the system 10 of FIG. 10A. The system 10 can include for example, an OCT, intravascular ultrasound (IVUS), or other intravascular imaging system. A stent 12 is shown in the blood vessel 5. The stent includes a plurality of struts. Some of the struts can generate shadows or shadow regions SR as part of the process of imaging the vessel with an intravascular probe. The system 10 can include various software modules suitable for performing side branch detection, stent detection, peak detection, shadow region detection and processing, error correction, indicator bar generation and display, model comparisons, lumen detection, and various other processes as described herein. Additional details relating to some exemplary stent detection features are described in more detail with regard to FIGS. 14A-18B. The system 10 can include a suitable light source that satisfies the coherence and bandwidth requirements of the applications and data collection described herein. The system 10 can include an ultrasound imaging system. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 11 such as an arterial lumen. The probe 7 can include a rotating or slidable fiber 15 that directs light forward into the lumen L or at a direction perpendicular to the longitudinal axis of the fiber 15. As a result, in the case of light that is directed from the side of the probe as the fiber 15 rotates, OCT data is collected with respect to the walls of the blood vessel 5. The walls of the blood vessel 5 define a lumen boundary. This lumen boundary can be detected using the distance measurements obtained from the optical signals collected at the probe tip 17 using lumen detection software component. Side branches and stent struts and shadow regions and other features can be identified in the scan lines generated during a pullback through the artery by the probe.

In one embodiment, the probe 7 can include other imaging modalities in addition to OCT such as ultrasound in one embodiment. In one embodiment, the lumen/lumen boundary refers to a portion of the vessel that is first impinged upon when light or ultrasound exists an intravascular imaging probe that generates a signal of interest for imaging the vessel. This excludes any blood flowing in the vessel which is typically removed using image processing in the form of masking. In one embodiment, the lumen or lumen boundary refers to a region of tissue that is disposed in front of the vessel wall and facing the blood containing region of the vessel.

Figure 10B:
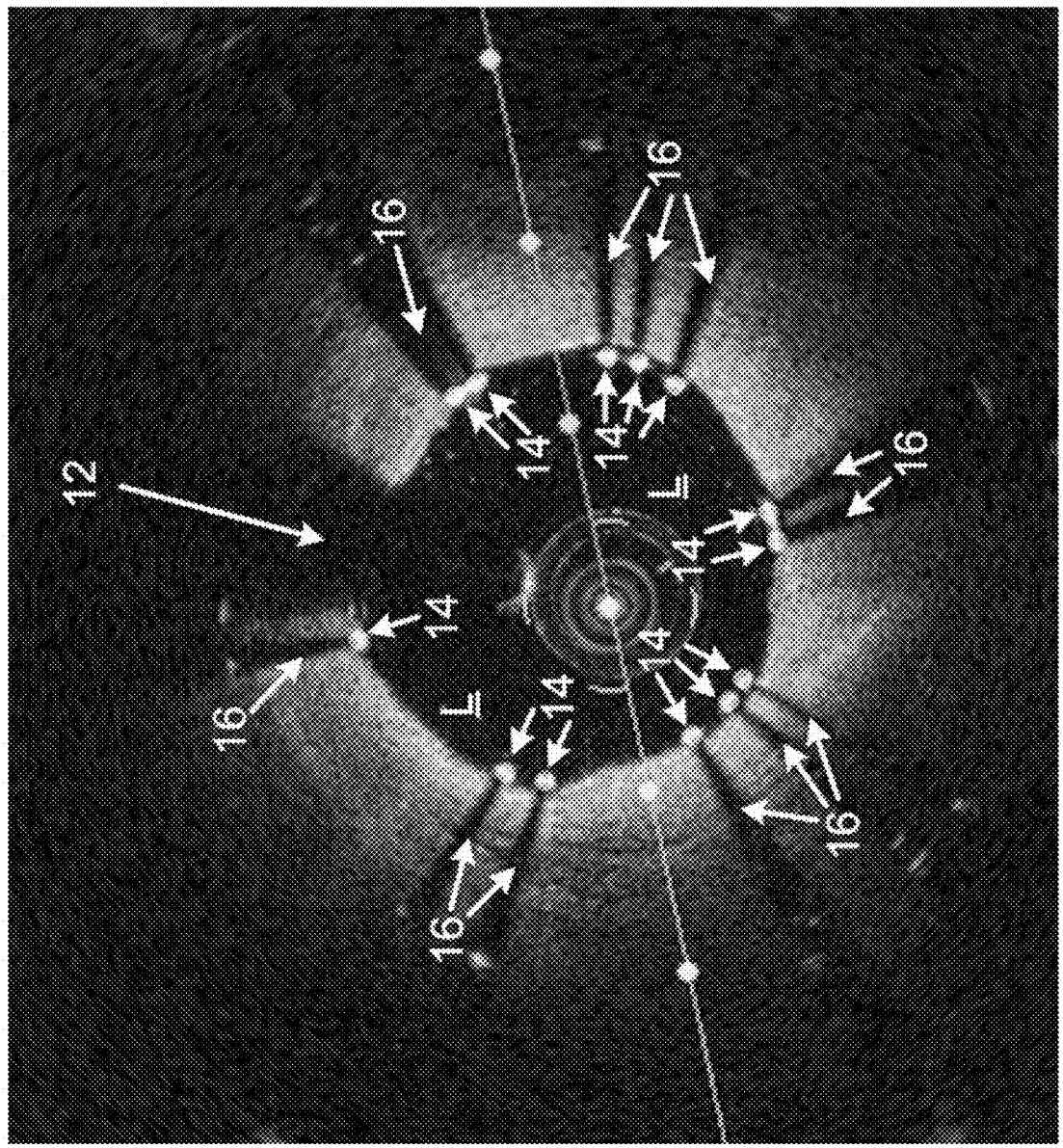
FIG. 10B is a cross-sectional OCT image of a stented blood vessel in accordance with an illustrative embodiment of the disclosure.

As shown in FIG. 10A, the probe tip 17 is positioned in the lumen L such that it is distal to a stented region of the blood vessel 5. The probe tip 17 is configured to transmit light and receive backscattered light from objects, such as for example stent 12, and the wall of the blood vessel 5. The probe tip 17 and the rest of the data collection probe 7 are pulled through the lumen L and the stented region. As shown in FIG. 10B, a probe 17 is shown prior to or after insertion in a blood vessel. The probe 7 is in optical communication with an OCT system 10. The OCT system or subsystem 10 that connects to probe 17 via an optical fiber 15 can include a light source such as a laser, an interferometer having a sample arm and a reference arm, various optical paths, a clock generator, photodiodes, and other OCT system components.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for side branch detection, stent strut candidate selection or identification, candidate stent strut shadow region detection, stent region detection, stent strut validation, correlations and comparisons of stent image data stent visualization, and pullback data collection as discussed below. In one embodiment, the software 44 can include a pipeline that includes various modules such as a stent detection module that is automated such that is operates on intravascular data to detect stent struts. The module can include various other software modules such as a sparse peak detection module, model strut generation module, false positive testing module, and others as described herein.

In one embodiment, the computing device 40 includes or accesses software modules or programs 44, such as a side branch detection module, a lumen detection module, a stent detection module, a stent strut validation module, a candidate stent strut identification module and other software modules. The software modules or programs 44 can include an image data processing pipeline or component modules thereof and one or more graphical user interfaces (GUI). The various software-based methods described herein can be included as part of the group of software/programs 44. The modules can be subsets of each other and arranged and connected through various inputs, outputs, and data classes. In one embodiment, the software modules 44 include a stent detection module such as an automated stent detection module.

An exemplary image processing pipeline and components thereof can constitute one or more software programs or modules 44. The software modules 44 may comprise several image processing algorithms tailored to detect the vessel lumen, side-branches, guide-wires, guide-catheters, stent struts and stent regions. This disclosure relates to image processing to determine the location of a metal strut within its shadow. The image data processing pipeline, its components software modules and related methods and any of the methods described herein are stored in memory and executed using one or more computing devices such as a processor, device, or other integrated circuit. The software modules or programs 44 receive image data and transform such image data into two dimensional and three dimensional views of blood vessels and stents and can include lumen detection software module, peak detection, stent detection software module, and side branch detection software modules and others.

As shown, in FIG. 10A, a display 46 can also be part of the system 10 for showing information 47 such as cross-sectional and longitudinal views of a blood vessel generated from OCT or IVUS imaging data and apposition bars and other indicators. The image processing software algorithms 44 provide data corresponding to detected image features such as stents, side-branches, guide-wire etc. and this data is input to the GUI where these features are displayed in a desired format on cross-sectional, longitudinal, and/or 3D display sections of the GUI.

In addition, the display 46 can also show information 47 such as cross-sectional and longitudinal views of a stented blood vessel generated using collected image data, user interfaces, images and various indicators and indicia. Representations of a stent, such as OCT or IVUS images thereof, can be shown to a user via display 46. Stent detection is performed prior to the display of these features and any coding or tagging with identifying indicia that may be included in the displayed image. This OCT-based information 47 can be displayed using one or more graphic user interface(s). The images of FIGS. 10B, 14A, 14B, and 18B and the other user interfaces and the components thereof depicted herein are examples of display information 47 that can be displayed and interacted with using a GUI and various input devices. Specifically, it shows a 2D cross-sectional view of a coronary artery containing a metal stent.

In addition, display information 47 can include, without limitation, cross-sectional scan data, longitudinal scans, diameter graphs, image masks, stents, areas of malapposition, lumen border, and other images or representations of a blood vessel or the underlying distance measurements obtained using an OCT system and data collection probe. The computing device 40 can also include software or programs 44, which can be stored in one or more memory devices 45, configured to identify stent struts and malapposition levels (such as based on a threshold and measured distance comparison), shadow regions, and struts within shadow regions and other blood vessel features such as with text, arrows, color coding, highlighting, contour lines, or other suitable human or machine readable indicia. Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in FIGS. 1B, 1C and 14A and 14B for example and as otherwise described and depicted herein.

FIG. 10B is a cross-sectional OCT image of a stented blood vessel, in accordance with the present disclosure. The lumen/lumen boundary L of the blood vessel is in the center of the image. The guide wire shadow 12 is visible at the top of the image, from 12 to 1 o'clock. Also visible in FIG. 10B are multiple metal stent struts 14, which cast shadows 16 in the OCT image. Metal stent struts cast shadows against the blood vessel wall because the coherent light typically used for OCT imaging cannot penetrate stent struts but is reflected. The present disclosure provides enhanced methods for detecting the precise offset of struts within strut shadows. Once detected, the shadows and struts of FIG. 10B can be used to generate the user interfaces and indicators described herein.

Figure 11:
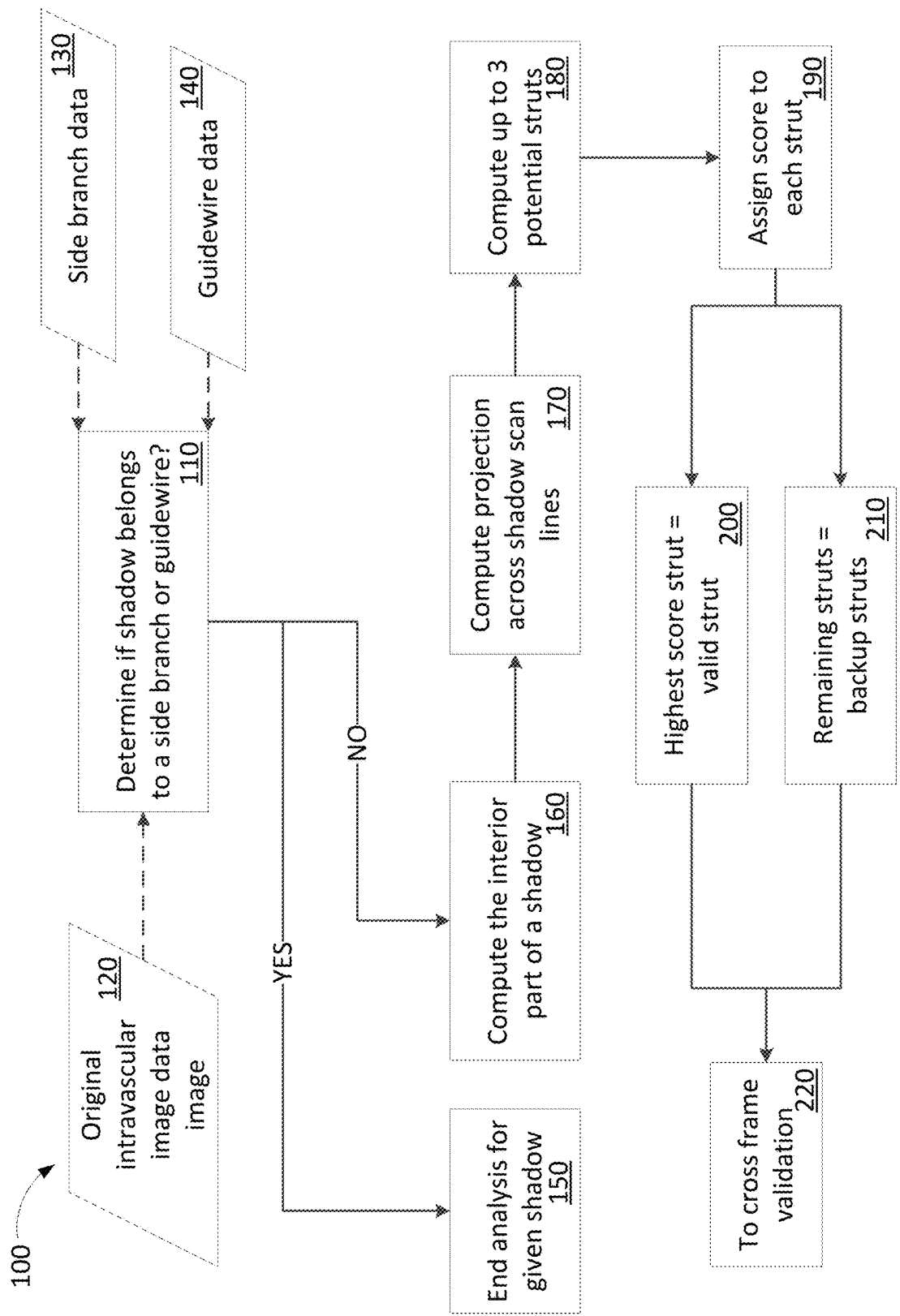
FIG. 11 is a process flow chart for detecting struts in OCT image data in accordance with an illustrative embodiment of the disclosure.

FIG. 11 is a process flow chart for detecting struts in OCT image data. The method 100 analyzes shadows corresponding to stent struts in a plurality of OCT pullback frames. The method 100 can include one or more of the steps described herein. Unless otherwise required, the steps can be performed in any order. The metal strut detection method operates upon various inputs from other image/intravascular data processing modules such as information about guide-wire (140), side-branch (130) and strut shadow locations (110). The process flow and associated method steps and stages can operate upon original intravascular data or raw data 120 obtained using a OCT, IVUS, or other intravascular data collection system. In one embodiment, data 120 has been processed by one or more image processing modules in a pipeline configuration.

In Step 110, each shadow in the OCT image data is compared or correlated with data inputs from a side branch detection module 130 and a guide-wire detection module 140 to determine if the shadow is attributable to a side branch vessel or guidewire. Methods, systems, and devices for detecting strut shadows, side branches, and pidewire shadows are known. See, e.g., U.S. Pat. Nos. 8,412,312; 8,478,387; 8,831,321; 9,138,147 and 9,173,591.

At Step 150, if a given shadow is determined to be attributable to the guidewire or a side branch, the shadow is discarded and the analysis ends with respect to that shadow. At Step 160, if a given shadow is determined to be attributable to a stent strut, either by direct detection or by process of elimination, the shadow is analyzed to compute, or isolate, the interior part of the shadow. The shadow boundaries are trimmed away or otherwise reduced or constrained such that only the scan lines, or A-Lines, corresponding to the interior (and hence the "darkest") portion of the shadow are retained. The reason for this is that the shadow region, specifically the start and stop scan lines of the shadow, can sometimes contain spillage from the neighboring lumen pixels. Isolating the interior of the shadow and ignoring transitionary scan lines at the shadow margins improves assessment of strut offsets.

At step 170, the shadow interior is analyzed to compute the projection (or sum) of each sample across scan lines corresponding to the interior part of the shadow. Each scan-line is sampled into discrete pixels or "samples". In the input OCT image data, each scan line refers to data acquired along a particular angular direction with the imaging catheter at the center. Each scan line is in turn radially sampled into a discrete set of pixels or "samples". Each sample in the OCT data is typically a few microns wide and is typically uniform in size. A "projection" refers to the process of adding across each scan line. In other words, the 2-dimensional shadow in the {scan-line, sample} space is collapsed into a 1-dimensional signal where the i-th index corresponds to the sum of the i-th sample of each scan-line involved in the process. The projection contains samples, at radius R, which are the average of samples from the constituent scanlines at that same radius R.

At step 180, the projection is searched for up to three (e.g., 1, 2, or 3) of the largest local maxima. The location, or offset, of each selected maximum may be noted as potential strut locations, and certain features of the selected maxima are then analyzed to determine which one is the best candidate for being a true strut. In various embodiments, only the largest maximum is selected. In other embodiments, two or three of the largest maxima are selected. The initial selection of multiple local maxima increases sensitivity. Although more than three local maxima can be selected, this typically is unnecessary because one of the three highest maxima usually indicates the true strut location. The maxima selection process is illustrated by FIGS. 12 and 13.

Figure 12:
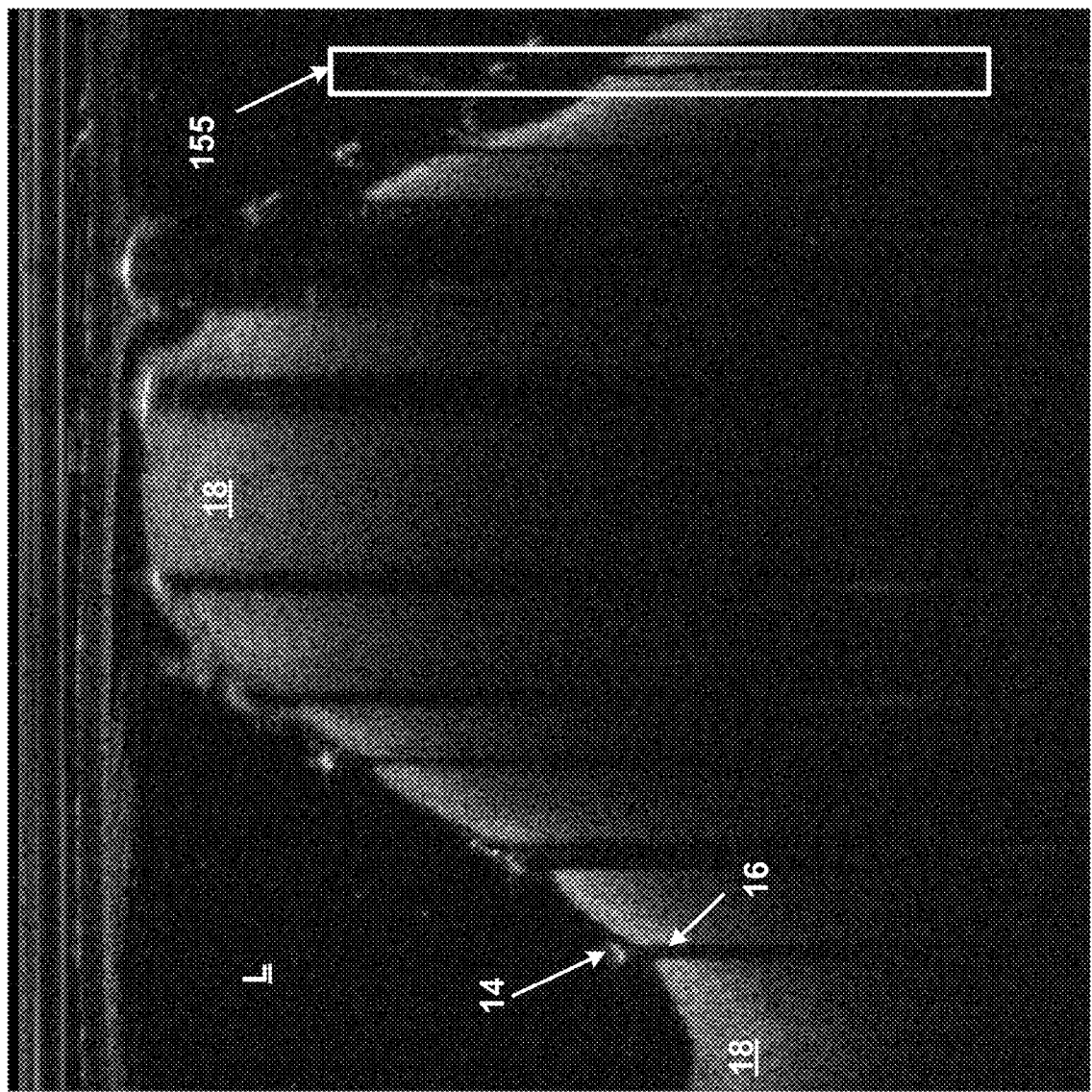
FIG. 12 is a scan line OCT image in polar co-ordinates, in log scale, of a stented vessel in accordance with an illustrative embodiment of the disclosure.

FIG. 12 is an A-Line or scan line OCT image, in log scale, of a stented blood vessel. The box 155 on the right of the image indicates a shadow under analysis, and FIG. 13 shows a projection graph for this shadow. The blood vessel lumen L is the dark region at the top of the image, and the blood vessel wall VW is the bright region at the bottom of the image. L is generally used to indicate the lumen herein. Multiple stents 14 and stent shadows 16 are visible in the image. In one embodiment, the lumen is the boundary between the tissue and the cleared interior of the vessel.

Figure 13:
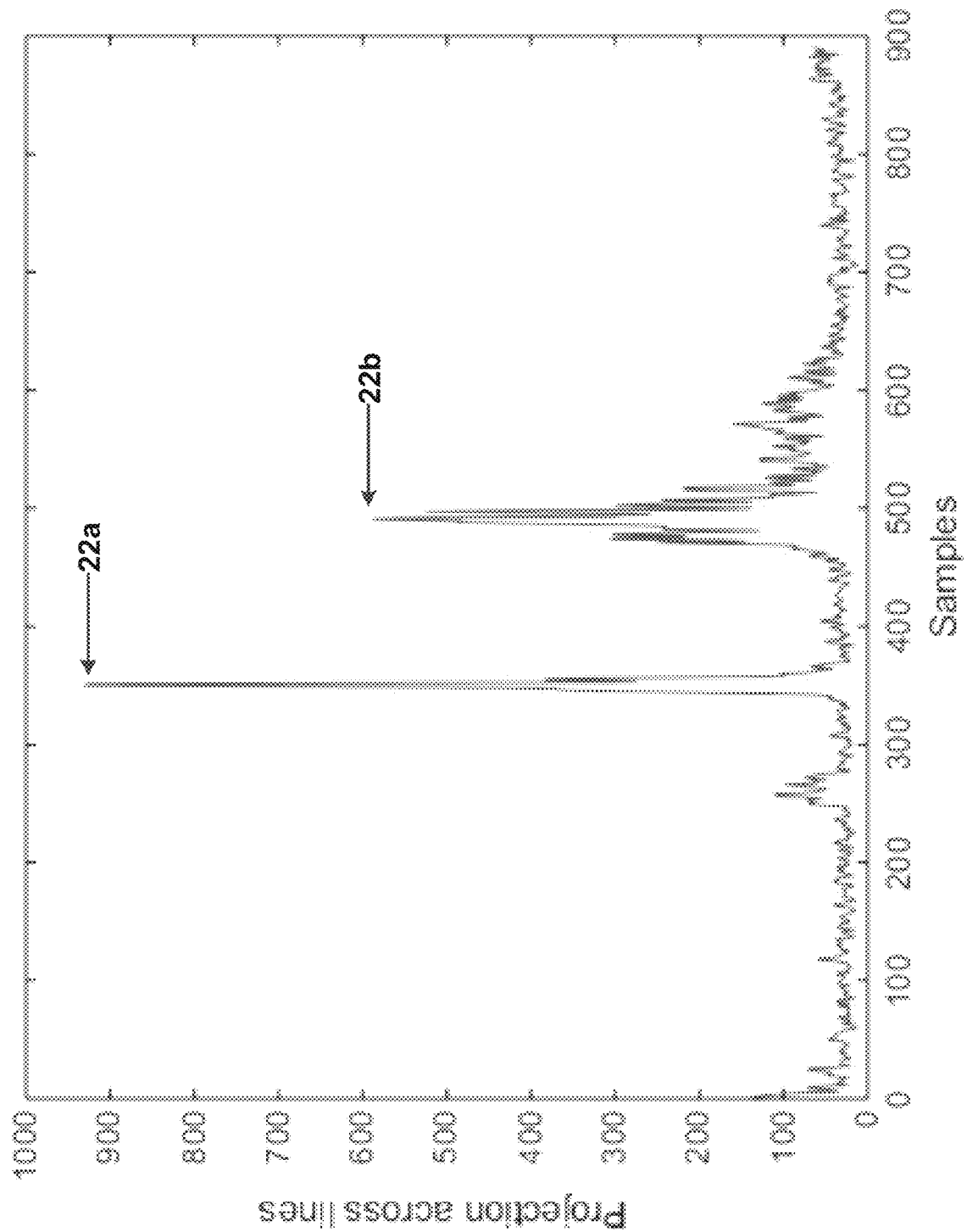
FIG. 13 is a graph illustrating detection of multiple potential struts within a surge shadow in accordance with an illustrative embodiment of the disclosure.

FIG. 13 is a graph illustrating detection of multiple potential struts within a single shadow. FIG. 13 is a plot of the projection across the interior shadow scan lines. There are two local maxima 22a and 22b. These maxima correspond to two potential strut locations within the shadow. These locations can be used by an intravascular imaging system such as an OCT or IVUS system to display stent struts on a user interface as shown herein.

Additional filters can be applied to the local maxima to remove false positives. In various embodiments, a local maximum is selected only if it has a signal greater than $1/10^{th}$ (i.e., 10%) of the global peak (largest maximum along the projection. The global peak is the peak with the greatest amplitude. The 10% threshold reduces the chance of selecting spurious local maxima due to noise. The threshold can be set between 5% (i.e., 1/20th) and 10% of the global peak, such as 5%, 6%, 7%, 8%, 9%, or 10%, with 10% being preferred. In various embodiments, if multiple peaks are detected in close proximity to each other, only the largest peak is selected for further analysis.

At Step 190, the selected local maxima are analyzed to determine which maximum has the highest probability of being the true strut based on the information available from the immediate neighborhood of the strut. A relative score is assigned to each strut based on one or more of the following criteria:

1. Proximity to lumen: The selected local maxima are scored based on proximity to the lumen boundary. The local maximum closest to the lumen around the strut shadow receives the highest score, and the local maximum farthest from the lumen around the strut shadow receives the lowest score.

2. Peak strength: The selected local maxima are scored based on peak strength. The local maximum with the highest peak receives the highest score, and the local maximum with the lowest peak receives the lowest score.

3. Degree of malapposition: The selected local maxima are scored based on their apposition, which refers to the state of being in juxtaposition to the lumen. Local maxima that are apposed within a predefined acceptable distance from the lumen or vessel wall receive a higher malapposition score. Struts that are too far away from the lumen or vessel wall (determined by a user specified threshold using one or more interface screens or based on accepted treatment thresholds) are penalized and receive a lower malapposition score as potential false positives. In one embodiment, a strut can either have a malapposition score of 0 or 1 depending on whether it is malapposed or not, respectively.

These scoring criteria are exemplary, and additional scoring criteria based on other strut and shadow features may be used. In one embodiment, candidate stent struts are validated using a cross-frame analysis to indicate that a strut is valid if a segment of strut is next to or aligned with another segment in an adjacent or neighboring frame.

Each local maxima gets a combined score which is the linear sum of the abovementioned criteria. At Step 200, the local maximum with the highest score is selected as the valid strut. At Step 210, the remaining local maxima are saved as alternative or backup struts pending further analysis. In the event of a tie, the local maximum closest to the lumen and/or the brightest local maximum are used as tiebreakers. Table 1 provides an exemplary ranking of local maxima for a stent shadow.

TABLE 1

Local maxima ranking for a stent shadow.

|  | Local Maximum 1 | Local Maximum 2 | Local Maximum 3 |
| --- | --- | --- | --- |
| Proximity to Lumen | 3 | 2 | 1 |
| Peak Strength | 2 | 1 | 3 |
| Malapposition | 1 | 0 | 0 |
| Total | 6 | 3 | 4 |

As shown in Table 1, local maximum 1 has the highest total score and therefore would be selected as the candidate valid strut. Local maxima 2 and 3 would be designated as backup struts.

At Step 220, all local maxima (valid strut and any backup struts) undergo multi-frame validation. In this step, adjacent frames are compared to verify that a valid strut in one frame aligns with valid struts selected for adjacent frames. If a valid strut does not aligns with other cross-frame struts, then the valid strut may be replaced by a backup strut if the backup strut better fits the cross-frame model. One embodiment of the multi-frame validation step can use stent strut geometry and location information. Other embodiments with a larger set of strut and shadow features can also be used for this step. That is location and geometry can be used as features all with other features such as prior pullback data or other user supplied information.

Once detected, the valid or chosen struts can be displayed on a user interface, which conveys vital visual aid to the clinician about the precise location of stent struts and whether adjustments may be necessary to optimize and/or speed-up stent placement and reduce the risk of side effects. The user interface can include cross-sectional images, L-Mode images, scan line images, three dimensional renderings, or any other suitable display format for visualizing detected struts. The user interface can also include the indicator bars, angiography data, and other views and features described and depicted herein.

The detection algorithm accurately identified the location of struts, with a sensitivity of that ranges from greater than about 80% in one embodiment. The detection algorithm accurately identified the location of struts, with a sensitivity of that ranges from greater than about 00% in one embodiment. In one embodiment, sensitivity is the proportion of struts correctly located over the total number of struts (struts correctly located plus struts missed). The positive predictive value is the proportion of struts correctly detected over all positive calls (struts correctly detected plus false positive in one embodiment. The various features described herein are suitable for use with different cath lab systems such as intravascular imaging and pressure measurement systems. The indicators and detection steps described herein offer various advantages to diagnosticians and those planning stent deployments or evaluating deployed stents.

In part, the invention provides computer-based methods, systems, and devices for detecting and displaying a stented region. In particular, the invention can identify the first and last frames of a stented region. A frame, in this context, refers to a cross-section through the vessel being imaged via OCT. The stented region is identified by iteratively processing OCT image frames to determine whether frames and/or a neighborhood of frames show features consistent with an expected configuration of stent struts. Stent struts appear in OCT images as solid structures, which are distinguishable from soft tissues, such as a blood vessel wall. In addition, the struts of a properly inflated stent typically are located adjacent the blood vessel wall. Thus, in a cross section of stented blood vessel, a plurality of stent struts would be distributed uniformly around the circumference of the vessel wall. Thus, frames exhibiting OCT features consistent with a deployed stent—e.g., a plurality of struts distributed around the entire vessel wall—are candidates for being designated as stent-containing frames.

In OCT imaging data, artifacts due to uncleared blood cells or catheter walls can have similar optical properties as stent struts. These imaging artifacts can often be interpreted by software as stent struts. However, background noise typically does not have the regular geometry of stents, which are composed of a meshwork of struts. For example, uncleared blood cells may be clustered in a single region, may be distributed randomly, and/or may not be positioned adjacent a vessel wall. The challenge is to distinguish frames that contain stent struts from frames that contain only false positives due to artifacts and no stent struts.

Another challenge is distinguishing whether there is a valid stented region present in the OCT image date and, if so, correctly locating the first and last frame imaging frames containing the stent. In one embodiment, the methods described herein are applicable to metal stents and bioresorbable stents and other non-metal stents. In general, one or more embodiments of the disclosure provide methods to identify frames of an intravascular pullback and the associated representation displayed to an end user that accurately detects stent struts and also accurately identifies zones or regions of the blood vessel in which no stent is present.

Stent Detection Embodiments

In part, the invention provides computer-based methods, systems, and devices for detecting and displaying a stented region. In particular, the invention can identify the first and last frames of a stented region. A frame, in this context, refers to a cross-section through the vessel being imaged via OCT. The stented region is identified by iteratively processing OCT image frames to determine whether frames and/or a neighborhood of frames show features consistent with an expected configuration of stent struts. Stent struts appear in OCT images as solid structures, which are distinguishable from soft tissues, such as a blood vessel wall. In addition, the struts of a properly inflated stent typically are located adjacent the blood vessel wall. Thus, in a cross section of stented blood vessel, a plurality of stent struts would be distributed uniformly around the circumference of the vessel wall. Thus, frames exhibiting OCT features consistent with a deployed stent for e.g., a plurality of struts distributed around the entire vessel wall are candidates for being designated as stent-containing frames.

In OCT imaging data, artifacts due to uncleared blood cells or catheter walls can have similar optical properties as stent struts. These imaging artifacts can often be interpreted by software as stent struts. However, background noise typically does not have the regular geometry of stents, which are composed of a meshwork of struts. For example, uncleared blood cells may be clustered in a single region, may be distributed randomly, and/or may not be positioned adjacent a vessel wall. The challenge is to distinguish frames that contain stent struts from frames that contain only false positives due to artifacts and no stent struts.

Another challenge is distinguishing whether there is a valid stented region present in the OCT image date and, if so, correctly locating the first and last frame imaging frames containing the stent. In one embodiment, the methods described herein are applicable to metal stents and bioresorbable stents and other non-metal stents. In general, one or more embodiments of the disclosure provide methods to identify frames of an intravascular pullback and the associated representation displayed to an end user that accurately detects stent struts and also accurately identifies zones or regions of the blood vessel in which no stent is present.

FIG. 14A is an L-Mode, or longitudinal, display of a stented vessel region before elimination of false positive struts. The longitudinal display is a type of cross-sectional view. Distal (D) end is to the left and proximal (P) end is to the right of the vessel depicted in the L-mode image. The actual stented region 101 spans from about 12 mm to about 45 mm in the L-Mode image. A false positive region 15 is located immediately adjacent the actual stented region 101, from about 45 mm to about 52 mm in the L-Mode image. The false positive region 15 is caused by background noise that has similar optical properties as stent struts. For example, uncleared blood cells swirling in the imaging area sometimes appear as stent struts in OCT images.

A software program analyzing these imaging data typically includes the false positive region 15 as part of the stented region 101. As a result, the software program may determine that the first stented frame is around 12 mm and the last stented frame is around 52 mm Display of the false positive region 15 as part of the stented region 101 can lead to misinterpretation or confusion in understanding of the image by the clinician, which can further lead to failed intervention (e.g., failure to reposition a malapposed stent) or unnecessary procedures (e.g., repositioning a properly deployed stent).

FIG. 14B is an L-Mode display of a stented vessel region after elimination of non-stented region 15, in accordance with the invention. This invention does not detect individual false positive struts but rather looks at the distribution of detected struts over a fixed longitudinal neighborhood and assesses the location of the stented region. False positive stented regions 15 can be eliminated automatically, enabling detection of the actual stented region 101.

Figure 15A:
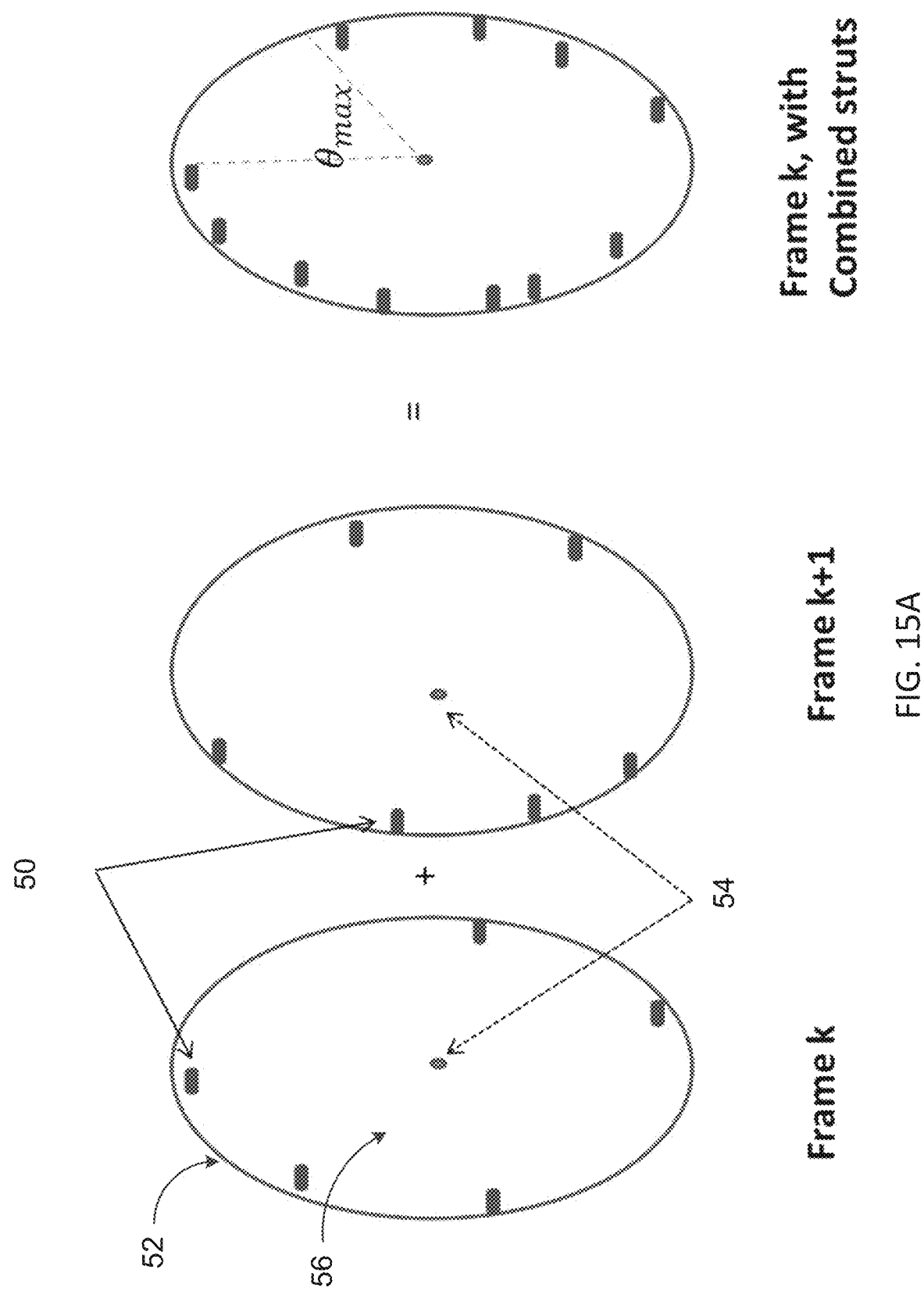
FIGS. 15A and 15B are diagrammatic depictions of combining frames as part of an evaluation of whether or not a frame is part of a stented region an automated stent detection algorithm in accordance with an illustrative embodiment of the disclosure.

FIG. 15A is a diagrammatic depiction of one embodiment of the stent region detection algorithm that creates a neighborhood of frames relative to frame being evaluated such as a frame k. In one embodiment, the neighborhood of frames can include two adjacent frames k and k+1 (or k and k−1) are used to analyze the strut angular coverage and geometry at frame k. The size and rules associated with selecting frames for a neighborhood can vary for a given application. In one embodiment, the stent region detection algorithm uses frames k−1, k and k+1 to accumulate struts and determine the max angular gap and subsequently the angular coverage metric. For a given neighborhood created relative to frame k, the set of frames on either side of k can be summed to create a super frame. A given super frame is an amalgamation of the struts on frame k and the other struts on the frames in the neighborhood.

In one embodiment, stent struts 50 are detected in OCT image data using known techniques and an estimate of the centroid 54 of the vessel wall is also pre-computed by known methods and used by the algorithm. If the stent is properly deployed and expanded, the stent struts typically will be adjacent the blood vessel wall 52 at the luminal boundary, but this method is equally applicable to frames where the stent deployment is not properly apposed against the lumen boundary (vessel wall). For a given frame k, we combine its struts with struts detected over a fixed neighborhood (in this embodiment, the neighboring frame k+1). The angular position of each strut is determined using the vessel centroid.

Figure 15B:
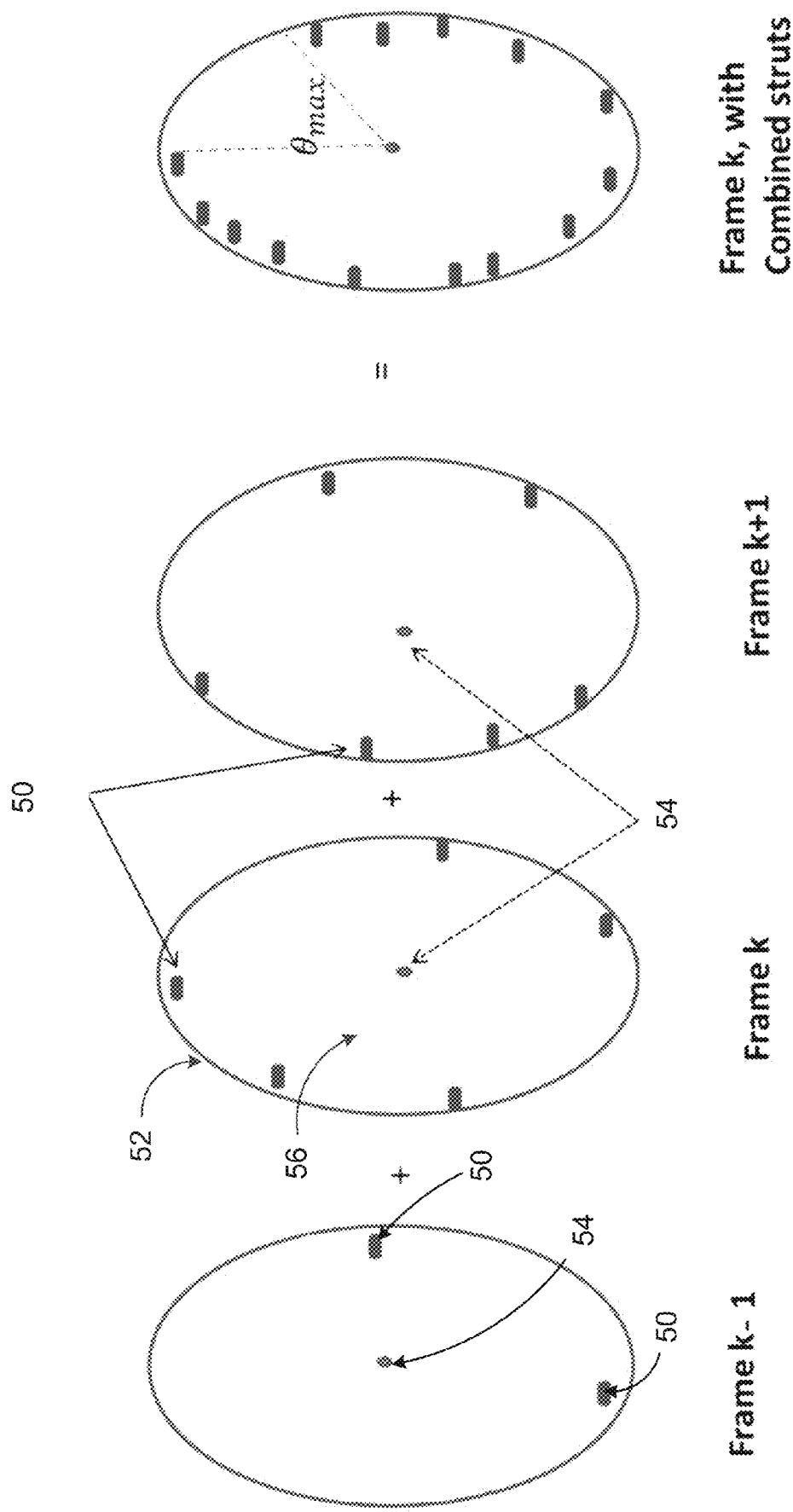

FIG. 15B is a diagrammatic depiction of another exemplary embodiment of the stent region detection algorithm where a neighborhood of frames is used to create a superframe or an amalgamation of struts for the neighborhood center on frame k. As shown it FIG. 15B, three adjacent frames k−1, k, and k+1 are used to analyze the strut angular coverage and geometry in a 3 frame neighborhood. As in FIG. 15A, stent struts 50 are detected in OCT image data using known techniques and an estimate of the centroid of the vessel wall is also pre-computed by known methods and used by the algorithm.

If the stent is properly deployed and expanded, the stent struts typically will be adjacent the blood vessel wall 52 at the luminal boundary, but this method is equally applicable to frames where the stent deployment is not properly apposed against the lumen boundary (vessel wall). For a given frame k, we combine its struts with struts detected over a fixed neighborhood (in this embodiment, the neighboring frames k−1 and k+1). The angular position of each strut is determined using the vessel centroid.

If a given frame belongs to a stented region, the frame should contain struts having close to a 360-degree coverage around the circumference of the blood vessel wall 52. Occasionally, struts are missed during the OCT imaging process, which would appear as a gap in coverage around the lumen. Thus, in a preferred embodiment, stent information from multiple frames is stacked or combined, and the gaps between struts in the combined data are then measured. Using struts detected over a neighborhood helps smooth the plot and use an easier thresholding method to separate the true stent regions from false positives. Also, presence of guide-wires and side-branches which manifest as large shadows in the image can lead to a lower angular coverage around the circumference. These features can be identified and can be accounted for when analyzing gaps between stent struts.

Referring again to FIGS. 15A and 15B, strut information from frame k is stacked or combined with stent information from frame k+1 to create multi-frame stent data. In the multi-frame analysis, the orientation of each frame is preserved, and the angular gap between struts is measured around the circumference of the vessel lumen in the multi-frame data. The largest angular gap between adjacent struts, $\theta_{max,k}$, is then computed relative to the vessel centroid for frame k.

FIG. 15A depicts a multi-frame analysis based on two adjacent frames, k and k+1. FIG. 15B depicts a multi-frame analysis based on three adjacent frames, k−1, k, and k+1. Combining struts from the adjacent frames brings in cross frame information to the stent region detection method. False positive struts will tend to be randomly distributed across a frame; therefore, frames and multi-frames containing only false positives are unlikely to show a uniform strut coverage around the circumference of the blood vessel. Hence, the largest angular gap for a valid stented frame or multi-frame is smaller, often much smaller, than the largest angular gap for a non-stented frame or multi-frame.

While larger neighborhoods can be used, the presence of false positives in larger neighborhoods can interfere with the approach. Thus, small neighborhood (e.g., 2-3 frames) are preferred. In various embodiments, the algorithm analyzes OCT data from a pullback to identify all frames and/or frame neighborhoods that contain a stent—i.e., where $\theta_{max,k}$ falls within a range values expected of a stented region. Using cross-frame and cross-neighborhood analyses, the algorithm determines the first and last stented frames of a stented region. False positives outside the stented region are revealed because the false positives are not contiguous with the stented region.

False positives around a stent end can be further eliminated by comparing the detected length of the stent to the known actual stent length. If the detected stent length exceeds the known stent length, the detection algorithm can be refined by either using a dynamic threshold to adjust the stent region or adjust the size of the neighborhood to give a better estimate of the stent region. The same approach can be applied to situations where the detected stent length is shorter than the known length.

The detection algorithm also can include a validation step that compares the detected stent geometry and length to a known stent geometry and length. Frames exhibiting atypical geometries can be eliminated as false positives and/or can be deprioritized until it is apparent that the atypical frame is part of a contiguous region of frames.

The detection algorithm is not limited to analyzing pairs of frames, but also can analyze stent information from a single frame, if the stent being imaged contains a sufficiently dense mesh network, or from more than two frames (e.g., 3, 4, 5, or more) if the stent being imaged contains a sparse mesh network. In addition, the frames used in the multi-frame analysis need not be adjoining frames but could be separated by a few frames. In one embodiment, this can be implemented using a sliding widow type algorithm.

Figure 16:
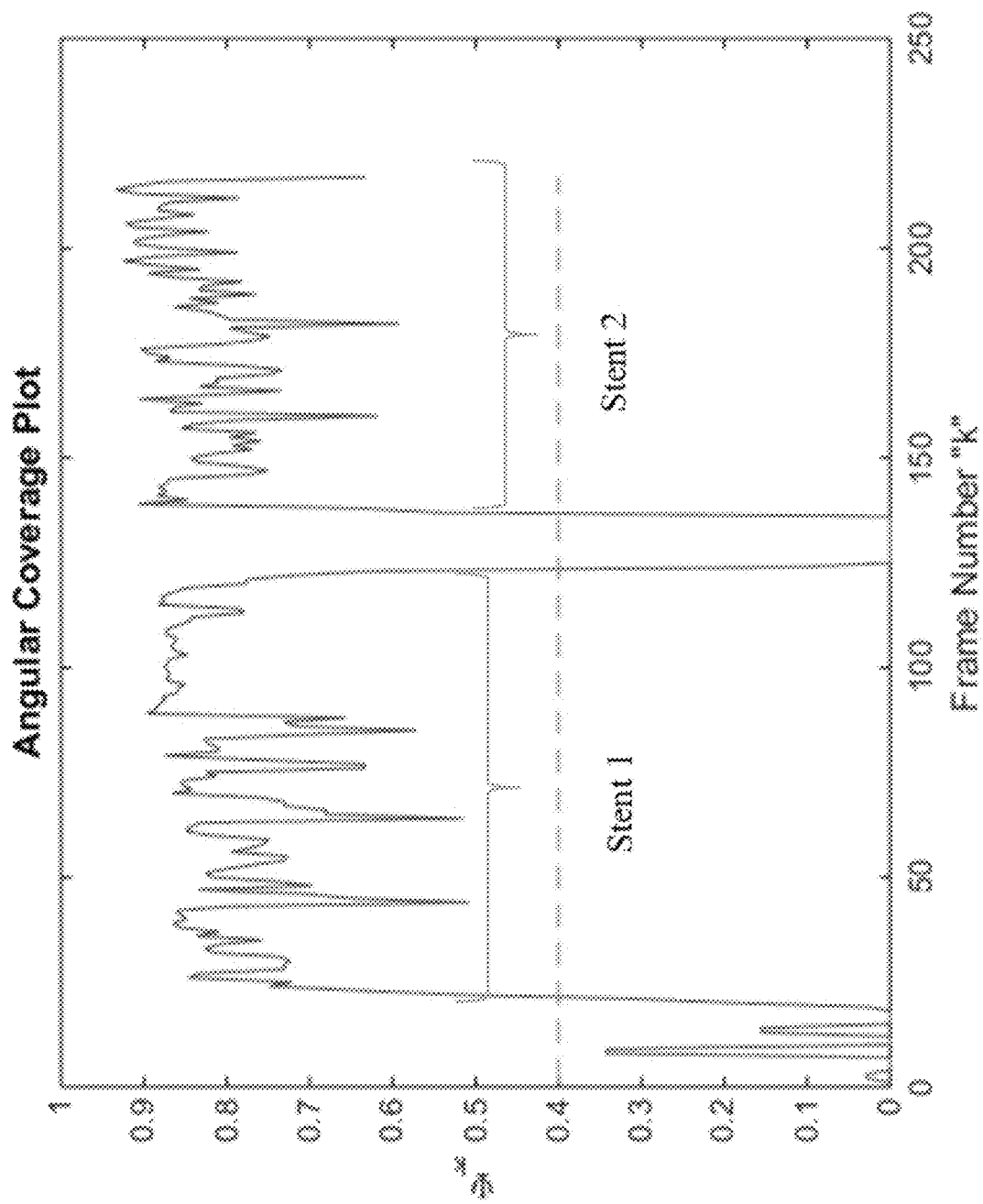
FIG. 16 is graph of an angular coverage plot demarcating the frame location of two stents in accordance with an illustrative embodiment of the disclosure.

The maximum angular gap is used to derive an angular coverage metric for each multi-frame, and the angular coverage metric can be plotted versus frame number on a graph. FIG. 16 is graph of an angular coverage plot demarcating the frame location of two stents within OCT pullback data. The angular coverage metric, $\Psi_k$ for frame k is defined by the following equation:

$$\Psi_k = 1 - \frac{\theta_{maxk}}{2\pi}$$

where $\theta_{max\ k}$ is the measured maximum angular gap for frame k. The measured maximum angular gap for frames k−1 and k+1 also are calculated. For each frame being evaluated using the stent region detection method, strut information from adjacent frames is combined. That said, the angular coverage metric is relative to the current frame k and applies to frame k even if a neighborhood of frames is summed and evaluated for coverage, the coverage result is generated for all of the frames in one embodiment. As angular gap size increases, the angular coverage metric decreases. In preferred embodiment, an angular coverage metric threshold is used to classify frames as either containing a stent or not.

A frame having an angular coverage metric below the predetermined threshold is categorized as a non-stented frame, whereas a frame having an angular coverage metric above the predetermined threshold is categorized as a stented frame. In a preferred embodiment, the angular coverage metric threshold is, for example, from about 0.25 to about 0.65. The angular coverage threshold can be automatically set or computed dynamically by the software, or it can be user defined, for example, depending on the geometry of particular stent. In one embodiment, about 0.8 is the angular coverage metric threshold value seen for some stents. In one embodiment, less than about 0.3 is the angular coverage metric threshold value seen when the frame k is outside of a stented region.

FIG. 16 is angular coverage plot for an illustrative OCT pullback. The angular coverage metric threshold is set at 0.4. The angular coverage metric is below 0.4 for frames 0 to 20; thus, these frames are categorized as non-stented frames by the algorithm. The angular coverage metric for frames 0 to 20 is less than zero, indicating potential background noise. Frames 20 to 125 have an angular coverage metric between 0.7 and 0.9, well above the threshold of 0.4. Frames 20 to 125 therefore are categorized as stented frames by the algorithm. The angular coverage metric drops sharply to zero after frame 125 and remains below the threshold until frame 140, indicating a non-stented region between frames 125 and 140. At frame 140, the angular coverage metric increases above the 0.4 threshold and remains above the threshold from frames 140 to 220. Thus, frames 140 to 220 are categorized as a stented region.

Figure 17:
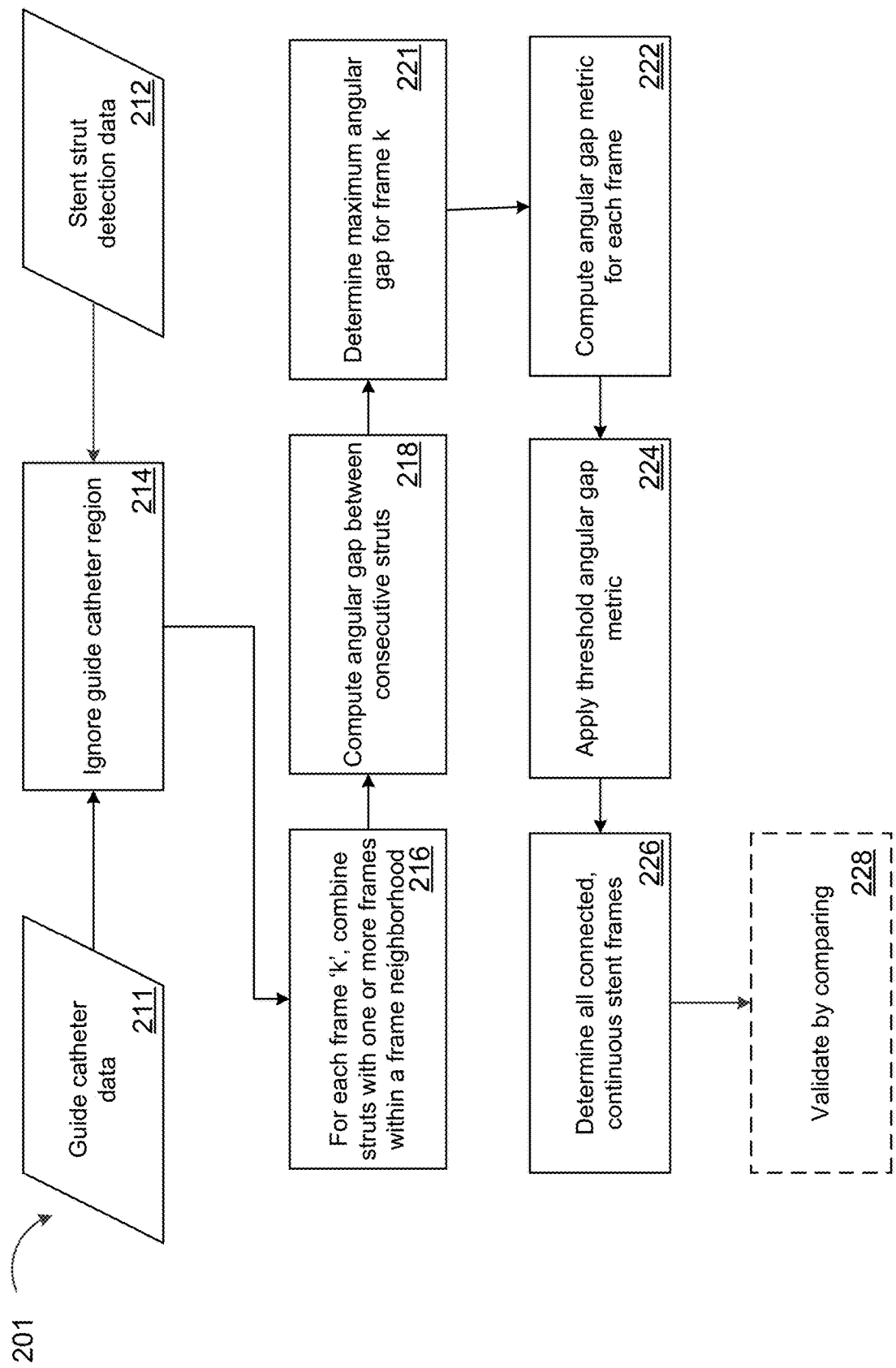
FIG. 17 is a flow chart showing a multi-frame stent region detection algorithm in accordance with an illustrative embodiment of the disclosure.

FIG. 17 is a flow chart showing a stent region detection algorithm 201. As will be appreciated, additional steps or analyses can be introduced without departing from base detection algorithm. The detection algorithm 200 receives guide catheter data 211 and/or stent strut detection data 212 obtained from preliminary analysis of OCT pullback data. These input data often are based on analysis of OCT scan lines or single OCT frames. At step 214, these input data are used to eliminate frames and/or stent strut detections in the guide catheter region. This step is optional but is preferred because the guide catheter often produces imaging artifacts that are misinterpreted as stent struts.

Next, at step 216, cross-frame or multi-frame information is generated by combining strut data from neighboring frames, k and k+1. In this way, the strut data for one frame that is near other frames in a neighborhood can be amalgamated, aggregated or combined to perform a type of cross-frame validation. In a preferred embodiment, frames k and k+1 are immediately adjoining OCT frames. In another embodiment, a neighborhood of 2n+1 frames can be used using frame set {k−n, k, k+1, . . . k−1, k, k+n−1, k+n}. For n=1, frames k−1, k and k+1 are used. However, as noted above, frame k struts can be combined with a data from a frame several microns apart. In addition, as noted above, the detection algorithm can analyze stent information from a single frame.

At step 218, the detection algorithm computes the angular gap between consecutive struts around the periphery of the vessel lumen in the multi-frame data. At step 221, the maximum angular gap for a given multi-frame is determined. The maximum angular gap is then used at step 222 to compute an angular gap metric for each frame, etc.). At step 224, the angular gap metric is then compared against a threshold angular gap metric. If the angular gap metric for a given multi-frame exceeds the threshold angular gap metric, then that multi-frame is flagged for inclusion in the actual stented region. Finally, at step 226, the detection algorithm determines, based on the multi-frame analysis, which OCT frames correspond to an actual stented region. Validation step 228 can be performed. The method can further include displaying an indicia relative to a region of a blood vessel indicative of a stented region. In general, any of the detected and validated struts can be displayed as described and depicted herein. Further, in one embodiment, the indicia is an apposition bar aligned with the stent region, wherein the apposition bar is rotationally agnostic or persistent.

Figure 18A:
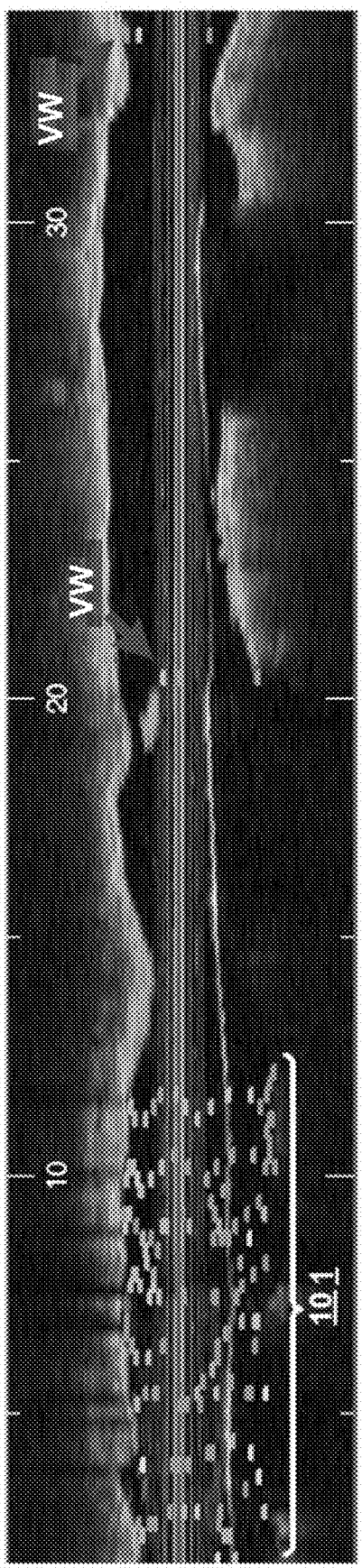
FIG. 18A is an intravascular image data representation user interface of a stented vessel region before elimination of false positive struts in accordance with an illustrative embodiment of the disclosure.
Figure 18B:
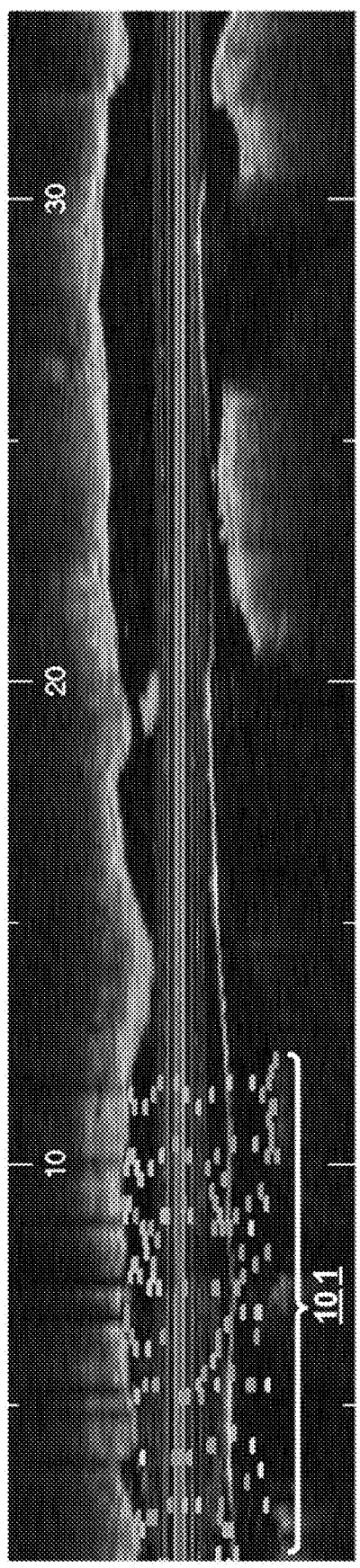
FIG. 18B is an intravascular image data representation user interface of a stented vessel region after elimination of false positive struts in accordance with an illustrative embodiment of the disclosure.

FIG. 18A is user interface representation showing a longitudinal or L-Mode display of a stented vessel region 101 before elimination of false positive struts 18. Multiple false positive struts were detected around 20 mm and around 34 mm FIG. 18B is an L-Mode display of a stented vessel region 101 after elimination of false positive struts. As shown in FIG. 18B, the detection algorithm eliminates false positive struts, resulting in a more accurate display of the actual stented region.

The use of arrow heads showing directionality in a given figure or the lack thereof are not intended to limit or require a direction in which information can flow. For a given connector, such as the arrows and lines shown connecting the elements shown in FIGS. 1 and 10A, for example, information can flow in one or more directions or in only one direction as suitable for a given embodiment. The connections can include various suitable data transmitting connections such as optical, wire, power, wireless, or electrical connections.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Non-Limiting Software Features and Embodiments for Implementing Interface, Detection and Other Features of Disclosure The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "indicating" or "detecting" or "measuring" or "calculating" or "comparing" "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages. In one embodiment, the software instructions are configured for operation on a microprocessor or ASIC of an intravascular imaging/data collection system.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system or used to generate a control signal or initiate a user interface command is implemented as a set of computer program instructions that is converted into a computer executable form, stored as such in a computer readable medium, and executed by a microprocessor under the control of an operating system.

Thus, query, response, transmitted probe data, input data and other data and signal described herein are transformed into processor understandable instructions suitable for responding to user interface selections, controlling a graphical user interface, control and graphic signal processing, displaying cross-sectional information and images from other data collection modalities, generating and displaying stents and apposition bars and other intravascular data, displaying OCT, angiography, detecting shadows, detecting peaks, and other data as part of a graphic user interface and other features and embodiments as described above. Data and parameters suitable for display as GUI components or controls, values, or as another representation in a graphical user interface can include without limitation malapposition values, apposition bars, stent struts, missing data representations, indicator bars, shadows, angiography representations, three and two dimensional renders and views, and other features as described herein.

Computer program logic implementing all or part of the functionality previously described herein may be embodied in various forms, including, hut in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed over a network.

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Prop ammable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, user interface data, control signals, angiography data, user actions, frequencies, interferometer signal data, detected stents, candidate stent struts, FFR data, IVUS data, shadows, pixels, intensity patterns, scores, projections, side branch data, and guidewire data and other information of interest as described herein.

Computers and computer systems described herein may include an operatively associated machine-readable medium such as computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The term "machine-readable medium" or "computer-readable-medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself ±10%, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

The invention claimed is:

1. A method of determining stent strut coverage in a blood vessel, the method comprising the steps of:
receiving optical coherence tomography data for a stented blood vessel, the optical coherence tomography data comprising a plurality of image frames;
storing the optical coherence tomography data in a memory device of an intravascular data collection system;
analyzing the plurality of image frames to identify stent struts on a per frame basis;
combining strut information from a neighborhood of frames of the plurality of image frames to create multi-frame data; and
determining, from the multi-frame data, a maximum angular gap between any two adjacent struts.

2. The method of claim 1, further comprising classifying a given frame as a stent-containing frame if the maximum angular gap is smaller than a threshold angular gap.

3. The method of claim 2, further comprising identifying zones that contain stents by identifying clusters of adjacent frames containing a maximum angular gap that is smaller than the threshold angular gap.

4. The method of claim 1, further comprising determining a centroid value for the blood vessel and computing the maximum angular gap relative to the centroid value for a given frame k.

5. The method of claim 1, wherein the maximum angular gap, $\theta_{max,k}$, for a given frame, k, is used to calculate an angular gap metric, $\Psi_k$, for frame k according to a formula $$\Psi_k = 1 - \frac{\theta_{maxk}}{2\pi}.$$

6. The method of claim 5, wherein an angular gap metric closer to 1 is indicative of the frame containing a stent.

7. The method of claim 6, further comprising the step of iteratively calculating the angular gap metric for successive neighboring frames.

8. The method of claim 5, further comprising sequentially classifying frames as a stent-containing frame if the angular gap metric for a given frame is larger than a threshold angular gap.

9. The method of claim 1, further comprising displaying an indicia relative to a region of the blood vessel indicative of a stented region.

10. The method of claim 9, wherein the indicia is an apposition bar aligned with the stented region, wherein the apposition bar is rotationally agnostic or persistent.

11. The method of claim 1, further comprising:
classifying a given frame as a stent-containing frame if the maximum angular gap is smaller than a threshold angular gap; and
aggregating neighboring stent-containing frames into a stented region comprising a first frame and a last frame.

12. The method of claim 11, further comprising terminating a first end of the stented region if a frame adjacent the first frame has an angular gap metric below the threshold angular gap.

13. The method of claim 11, further comprising terminating a second end of the stented region if a frame adjacent the last frame has an angular gap metric below the threshold angular gap.

14. The method of claim 1, further comprising displaying an indicia indicative of one or more regions in an intravascular image wherein image data was unavailable for display.

15. The method of claim 1, wherein an angular coverage metric is of the form $$\Psi_k = 1 - \frac{\theta_{maxk}}{2\pi},$$

wherein, $\theta_{max,k}$ is a largest angular gap between adjacent struts.

16. The method of claim 15, further comprising sequentially classifying frames as a stent-containing frame if the angular coverage metric for a given frame is larger than a threshold angular gap.

17. A method of determining stent strut coverage in a stented blood vessel, the method comprising the steps of:
storing, using an intravascular imaging system, one or more intravascular image datasets of the blood vessel, each intravascular dataset comprising a plurality of frames;
defining a neighborhood, the neighborhood comprising a frame k and one or more frames in vicinity of frame k;
determining a maximum angular gap for frame k by combining all of struts detected within all frames of the neighborhood; and
generating an angular coverage metric $\Psi_k$ with regard to frame k using the determined maximum angular gap.

18. The method of claim 17, wherein the angular coverage metric is of the form $$\Psi_k = 1 - \frac{\theta_{maxk}}{2\pi},$$

wherein, $\theta_{max,k}$ is a largest angular gap between adjacent struts.

19. A programmable processor-based computing device of an intravascular imaging system for detecting one or more stented regions, the programmable processor-based computing device comprising:
one or more data access channels to receive intravascular imaging data;
a processor and associated memory in electrical communication with the one or more data access channels, wherein the processor is programmed to:
store, using an intravascular imaging system, one or more intravascular image datasets of the blood vessel, each intravascular dataset comprising a plurality of frames;
define a neighborhood, the neighborhood comprising a frame k and one or more frames in vicinity of frame k;
determine a maximum angular gap for frame k by combining struts detected within all frames of the neighborhood;
generate an angular coverage metric $\Psi_k$ with regard to frame k using the determined maximum angular gap; and
classify frames as a stent-containing frame if the angular coverage metric for a given frame is larger than a threshold angular gap metric.

20. The programmable processor-based computing device of claim 19 wherein the angular coverage metric is of the form $$\Psi_k = 1 - \frac{\theta_{maxk}}{2\pi},$$

wherein, $\theta_{max,k}$ is a largest angular gap between adjacent struts.

* * * * *